(12) United States Patent
Li

(10) Patent No.: US 11,007,253 B2
(45) Date of Patent: May 18, 2021

(54) METHOD FOR PREVENTING OR TREATING RADIATION AND CHEMICAL DAMAGE

(71) Applicant: Talengen International Limited, Discovery Bay (HK)

(72) Inventor: Jinan Li, Shenzhen (CN)

(73) Assignee: Talengen International Limited, Discovery Bay (HK)

( * ) Notice: Subject to any disclaimer, the term of this patent is extended or adjusted under 35 U.S.C. 154(b) by 59 days.

(21) Appl. No.: 16/062,421

(22) PCT Filed: Dec. 16, 2016

(86) PCT No.: PCT/CN2016/110455
§ 371 (c)(1),
(2) Date: Jun. 14, 2018

(87) PCT Pub. No.: WO2017/101873
PCT Pub. Date: Jun. 22, 2017

(65) Prior Publication Data
US 2019/0060420 A1    Feb. 28, 2019

(30) Foreign Application Priority Data

Dec. 18, 2015    (WO) ................ PCT/CN2015/097949

(51) Int. Cl.
| *A61K 38/48* | (2006.01) |
| *A61K 38/00* | (2006.01) |
| *A61P 39/00* | (2006.01) |
| *A61K 45/06* | (2006.01) |

(52) U.S. Cl.
CPC ............ *A61K 38/484* (2013.01); *A61K 38/00* (2013.01); *A61K 45/06* (2013.01); *A61P 39/00* (2018.01); *C12Y 304/21007* (2013.01)

(58) Field of Classification Search
CPC ...... A61K 38/484; A61K 38/00; A61K 45/06; A61P 39/00; C12Y 304/21007
See application file for complete search history.

(56) References Cited

U.S. PATENT DOCUMENTS

| 3,434,929 | A |   | 3/1969 | Buck |
| 4,245,051 | A |   | 1/1981 | Reich et al. |
| 6,057,122 | A | * | 5/2000 | Davidson ............. C12N 9/6435 435/68.1 |
| 10,709,771 | B2 |   | 7/2020 | Li |
| 2002/0103129 | A1 |   | 8/2002 | Ge et al. |
| 2002/0159992 | A1 |   | 10/2002 | Henkin et al. |
| 2003/0014876 | A1 |   | 1/2003 | Goldie |
| 2003/0147876 | A1 |   | 8/2003 | Ni et al. |
| 2004/0192640 | A1 |   | 9/2004 | Gori et al. |
| 2005/0250694 | A1 |   | 11/2005 | Ma |
| 2010/0099600 | A1 |   | 4/2010 | Ny et al. |
| 2010/0184661 | A1 |   | 7/2010 | Luo et al. |
| 2011/0142819 | A1 |   | 6/2011 | Ny et al. |
| 2012/0114630 | A1 |   | 5/2012 | Zwaal |
| 2014/0205588 | A1 |   | 7/2014 | Zwaal |
| 2014/0273275 | A1 |   | 9/2014 | Jacobs et al. |
| 2018/0360930 | A1 |   | 12/2018 | Li |
| 2018/0369345 | A1 |   | 12/2018 | Li |
| 2019/0015485 | A1 |   | 1/2019 | Li |
| 2019/0060420 | A1 |   | 2/2019 | Li |
| 2019/0083586 | A1 |   | 3/2019 | Li |
| 2019/0151421 | A1 |   | 5/2019 | Li |
| 2019/0151422 | A1 |   | 5/2019 | Li |
| 2019/0247472 | A1 |   | 8/2019 | Li |

FOREIGN PATENT DOCUMENTS

| CN | 87104683 | A | 12/1988 |
| CN | 1135892 | A | 11/1996 |
| CN | 1585649 | A | 2/2005 |
| CN | 1643140 | A | 7/2005 |
| CN | 1768138 | A | 5/2006 |
| CN | 1961958 | A | 5/2007 |
| CN | 101171030 | A | 4/2008 |
| CN | 101563100 | A | 10/2009 |
| CN | 101573134 | A | 11/2009 |
| CN | 101628113 | A | 1/2010 |
| CN | 102121023 | A | 7/2011 |
| CN | 103656630 | A | 3/2014 |
| CN | 103764163 | A | 4/2014 |
| CN | 104914247 | A | 9/2015 |
| JP | 2002512006 | A | 4/2002 |
| JP | 2005519992 | A | 7/2005 |
| JP | 2005525798 | A | 9/2005 |
| JP | 2009502985 | A | 1/2009 |
| JP | 2010502600 | A | 1/2010 |

(Continued)

OTHER PUBLICATIONS

Lyer et al., Indian J Plast Surg, 2012, vol. 45, No. 2, p. 325-331.*
Score Search results, conducted on Jan. 17, 2020, 6 pages of PDF.*
U.S. Appl. No. 16/062,389, filed Jun. 14, 2018, Jinan Li , Shenzhen.
U.S. Appl. No. 16/062,410, filed Jun. 14, 2018, Jinan Li , Shenzhen.
U.S. Appl. No. 16/063,569, Jinan Li , Shenzhen.
U.S. Appl. No. 16/063,534, Jinan Li , Shenzhen.
U.S. Appl. No. 16/062,037, Jinan Li , Shenzhen.
U.S. Appl. No. 16/062,049, Jinan Li , Shenzhen.
U.S. Appl. No. 16/062,052, Jinan Li , Shenzhen.
Andreasen, P. et al., "The Urokinase-Type Plasminogen Activator System in Cancer Metastasis: A review:," Int. J. Cancer, vol. 72: 1-22 (1997).
Cai, W et al. "The anti-angiogenesis effect of plasminogen kringle 5" Progress in Physiological Sciences, vol. 35 (2):159-162 (2004).
Collen, D. et al., "Basic and Clinical Aspects of Fibrinolysis and Thrombolysis," Blood, vol. 78 (12):3114-3124 (1991).

(Continued)

*Primary Examiner* — Kade Ariani
(74) *Attorney, Agent, or Firm* — Nelson Mullins Riley & Scarborough LLP; Jill Gorny Sloper, Esq.

(57) ABSTRACT

The present invention relates to use of plasminogen in prevention, treatment, amelioration and/or elimination of radiation and chemical damage and related diseases in a subject, and further provides a novel therapeutic strategy for treating different types of radiation and chemical damage.

7 Claims, 5 Drawing Sheets

Specification includes a Sequence Listing.

(56) References Cited

FOREIGN PATENT DOCUMENTS

| | | |
|---|---|---|
| JP | 2010-515694 A | 5/2010 |
| JP | 2015505326 A | 2/2015 |
| WO | 9950413 A2 | 10/1999 |
| WO | 00/18436 A1 | 4/2000 |
| WO | 2003066842 A3 | 8/2003 |
| WO | 2007009382 A1 | 1/2007 |
| WO | 2008026999 A2 | 3/2008 |
| WO | 2008117767 A1 | 10/2008 |
| WO | 2009093540 A1 | 7/2009 |
| WO | 2010136059 A1 | 12/2010 |
| WO | 2013049697 A1 | 4/2013 |
| WO | 2015023752 A1 | 2/2015 |
| WO | 2015026494 A2 | 2/2015 |
| WO | 2017/101866 A1 | 6/2017 |
| WO | 2017/101867 A1 | 6/2017 |
| WO | 2017/101868 A1 | 6/2017 |
| WO | 2017/101869 A1 | 6/2017 |
| WO | 2017/101870 A1 | 6/2017 |
| WO | 2017/101871 A1 | 6/2017 |
| WO | 2017/101872 A1 | 6/2017 |
| WO | 2017/101873 A1 | 6/2017 |

OTHER PUBLICATIONS

Collen, D. et al., "Ham-Wasserman Lecture Role of the Plasminogen System in Fibrin-Homeostasis and Tissue Remodeling," American Society of Hematology, 9 pages (2001).

Cui, F. et al., "Role of the Molecular Pathogenetic Mechanism of Plasminogen Activator-1 (PAI-1) in Fibrostic Remodeling of Radiated Renal", Chinese Clinical Rehabiliation, vol. 7(12):1768-1769 (2003).

Davalos, D. et al., "Fibrinogen as a key regulator of inflammation in disease," Semin Immunopathol., vol. 34:43-62 (2012).

Hay, E. et al., Cell Biology of Extracellular Matrix, Second Edition, 1991, 15 pages.

He, C. et al., "Tissue cooperation in a proteolytic cascade activating human interstitial collagenase," PNAS, vol. 86: 2632-2636 (1989).

Hou, W. et al., "Preparation of Human Recombinant Kringle and Bioactivity," Hereditas, vol. 27 (4):617-622 (2005).

Hunt, J. et al., "Simplified recombinant plasmin: Production and functional comparison of a novel thrombolytic molecule with plasma-derived plasmin," Thromb Haemost., vol. 100: 413-419 (2008).

International Search Report, PCT/CN2016/110455, dated Mar. 9, 2017, 14 pages.

Jin, G.H. et al., "Combination of Human Plasminogen Kringle with Ionizing Radiation Significantly Enhances the Efficacy of Antitumor Effect", Int. J. Cancer., vol. 121: 2539-2546 (2007).

Le, J. et al. "Obstetrics and Gynecology, edition 7", People's Medical Publishing House, Jan. 31, 2008 (Jan. 31, 2008), introduction.

Li, Z. et al., "Advances in Studies on Treatment for Hepatic Fibrosis", Journal of Liaoning Medical Universty, vol. 28 (2):46-48 (2007).

Liu, M. et al., "Plasminogen: Structure, Function and Evolution", Journal of Ocean University of China, vol. 40 (10):69-74 (2010).

Lu, X.et al. "Antitumor Activity of Recombinant K1-3 Domain of Human Plasmihogen" Amino Acids and Biotic Resources, vol. 27(2):55-57 (2005).

Marder, V.J. et al., "Direct fibrinolytic agents: biochemical attributes, preclinical foundation and clinical potential," Journal of Thrombosis and Haemostasis, vol. 8: 433-444 (2010).

Mignatti, P. et al., "Biology and chemistry of proteinases in tumor invasion," Physiol Rev., vol. 73: 161-185 (2014).

Nagai, N. et al., "Recombinant human microplasmin: production and potential therapeutic properties," Journal of Thrombosis and Haemostasis, vol. 1: 307-313 (2002).

Pohl, J., et al., "Plasminogen Deficiency Leads to Impaired Lobular Reorganization and Matrix Accumulation after Chronic Liver Injury," American Journal of Pathology, vol. 159(6):2179-2186 (2001).

Raum, D., et al., "Synthesis of Human Plasminogen by the Liver," Science, vol. 208(4447): 1036-1037 (1980).

Rifkin, D. et al., "Proteolytic control of growth factor availability," APMIS, vol. 107: 80-8 (1999).

Rifkin, D.B., "Growth factor control of extracellular proteolysis," Cell Differentiation and Development, vol. 32: 313-318 (1990).

Ryu, J-K. et al., "Blood coagulation protein fibrinogen promotes autoimmunity and demyelination via chemokine release and antigen presentation," Nature Communications, vol. 6 (8164) 15 pages (2015).

Saksela, O. et al., "Cell-Associated Plasminogen Activation: Regulation and Physiological Functions," Ann. Rev. Cell Bioi., vol. 4: 93-126 (1988).

Shen, Y. et al., "Plasminogen is a Key Proinflammatory Regulator that Accelerates the Healing of Acute and Diabetic Wounds," Blood., vol. 119 (24):5879-5887 (2012).

Sottrup-Jensen, L. et al., "Amino-acid sequence of activation cleavage site in plasminogen: Homology with"pro" part of prothrombin," PNAS, vol. 72 (7): 2577-2581 (1975).

Stoppelli, M. et al., "Differentiation-enhanced binding of the amino-human urokinase plasminogen activator to a specific receptor on U937 monocytes," PNAS, vol. 82:4939-4943 (1985).

Takamura, T. et al., "Genes for systemic vascular complications are differentially expressed in the livers of Type 2 diabetic patients," Diabetologia, vol. 47: 638-647 (2004).

Tyagi, S., "Proteinases and myocardial extracellular matrix turnover," Molecular and Cellular Biochemistry, vol. 168: 1-12 (1997).

Valvil, D. et al., "Fibrinogen, chronic obstructive pulmonary disease (COPD) and outcomes in two United States cohorts," International Journal of COPD, vol. 7, 173-182 (2012).

Vassall, J-D., et al., "A Cellular Binding Site for the MR 55,000 Form of the Human Plasminogen Activator, Urokinase," The Journal of Cell Biology, vol. 100: 86-92 (1985).

Werb, Z. et al., Endegenous Activation of Latent Collagenase by Rheumatoid Synovial Cells, The New England Journal of Medicine, vol. 296(18): 1017-1023 (1977).

Wiman, B. et al., "Structural Relationship between "Glutamic Acid" and "Lysine" Forms of Human Plasminogen and Their Interaction with the NH,-Terminal Activation Peptide as Studied by Affinity Chromatography," Eur. J. Biochem., vol. 50: 489-494 (1975).

Xie, X. et al. "Obstetrics and Gynecology, edition 8", People's Medical Publishing House, Mar. 31, 2013 (Mar. 31, 2013), p. 256.

Yu, D. et al., "Measurements of Plasmin-Alpha2 Antiplasmin Complex in Patients with Liver Cirrhosis and Hepatocarcinoma," Laboratory Medicine and Clinic, vol. 6 (2): 92-93 (2009).

U.S. Appl. No. 16/062,037, Oct. 4, 2019, 79492-20001.00.
U.S. Appl. No. 16/062,049, Oct. 4, 2019, 79492-20001.00.
U.S. Appl. No. 16/062,052, Nov. 18, 2019, 79492-20003.00.
U.S. Appl. No. 16/062,410, Oct. 29, 2019.
U.S. Appl. No. 16/062,389, Oct. 7, 2019.
U.S. Appl. No. 16/062,389, Jul. 31, 2019.
U.S. Appl. No. 16/063,534, Nov. 18, 2019, C6222-001.

Bezerra, J. et al., "Plasminogen deficiency leads to impaired remodeling after a toxic injury to the liver," PNAS, vol. 96(26):15143-15148 (1999).

International Search Report, PCT/CN2016/110451, dated Feb. 16, 2017, 12 pages.

International Search Report, PCT/CN2016/110454, dated Mar. 13, 2017, 14 pages.

Okada, K. et al., "Binding of plasminogen to hepatocytes isolated from injured mice liver and nonparenchymal cell-dependent proliferation of hepatocytes," Blood Coagulation and Fibrinolysis, vol. 19:503-511 (2008).

Romagnuolo, R., et al., NP-000292.1, "plasminogen isoform 1 precursor," GenBank, Mar. 15, 2015.

Tanaka, K. et al, "Involvement of tissue line system in liver regenerating: Examination using plasminogen gene knockout mice," Journal of Japan Surgical Society, vol. 101:520, 3 pages (2000).

Vogten, J. M., et al., "Angiostatin inhibits experimental liver fibrosis in mice," International Journal of Colorectal Disease, vol. 19(4):387-394 (2004).

U.S. Appl. No. 16/062,037, Mar. 23, 2020.
U.S. Appl. No. 16/062,049, Mar. 23, 2020.

(56) References Cited

OTHER PUBLICATIONS

U.S. Appl. No. 16/062,052, Mar. 6, 2020.
U.S. Appl. No. 16/062,389, Apr. 2, 2020.
U.S. Appl. No. 16/062,410, Mar. 2, 2020.
U.S. Appl. No. 16/063,534, May 11, 2020.
U.S. Appl. No. 16/063,569, Jun. 25, 2020.
U.S. Appl. No. 16/063,569, Feb. 24, 2020.
A. Richard Kitching et al, "Plasminogen and Plasminogen Activators Protect against Renal Injury in Crescentic Glomerulonephritis," J. Exp. Med, vol. 185(5):963-968 (1997).
Fisher, E.J. et al"Displacement of Tissue Bound Plasminogen by Glucose: A Possible Mechanism in the Pathogenesis of Diabetic Nephropathy," Endocrinology and Metabolism, vol. 14 (6):371-376 (1997).
Li et al., "Research Progress of Liver Fibrosis Treatment," Journal of Liaoning Medical College, vol. 28(2): 46-48 (2006).
Mitazaki, S. et al., "Interleukin-6 modulates oxidative stress produced during the development of cisplatin nephrotoxicity," Life Sciences, vol. 92:694-700 (2013).
Naoyuki Kawao et al., "Plasminogen Plays a Crucial Role in Bone Repair," J.Bone Miner.Res., vol. 28(7):561-1574 (2013).
NP-000292.1, plasminogen isoform 1 precursor[*Homo sapiens*], Gen-bank, Apr. 23, 2016.
Sima J et al., "The effect of angiostatin on vascular leakage and VEGF expression in rat retina" FEBS Lett, vol. 564(1-2):19-23 (2004).
Sun, Haiou, "Mechanism of Drug Induced Kidney Injury and Clinical Manifestations thereof," J Nephrol Dialy Transplant, vol. 15(3):252-257 (2006).
Zhang, S. et al., "Therapeutic Potential of Angiostatin in Diabetic Nephropathy," Journal of the American Society of Nephrology, vol. 17(2):475-486 (2006).
Zhao L. et al."Experimental Research on Radiation Protection Mecha-nism of Interleukin-6 (IL-6)" Acta Academiae Medicinae Xuzhou, vol. 25 (1): 6-8 (2005).
Aisina, R.B. et al., "Structure and Function of Plasminogen/Plasmin System," Russian Journal of Bioorganic Chemistry, vol. 40(6): 590-605 (2014).
Badylack, S. et al., The Beneficial Effect of Lys-Plasminogen upon the Thrombolytic Efficacy of Urokinase in a Dog Model of Peripheral Arterial Thrombosis, Haemostasis, vol. 21: 278-285 (1991).
Groeneveld, D. et al., "Intrahepatic fibrin(ogen) deposition drives liver regeneration after par-tial hepatectomy in mice and humans," Blood, vol. 133(11):1245-1256 (2019).
Iyer, S. et al., Management of Radiation Wound, Indian J Plast Surg., vol. 45(2): 325-331 (2012).
Kopec et al., "Role of Fibrin(ogen) in Progression of Liver Disease: Guilt by Association?" Semin Thromb Hemost. vol. 42(4):397-407 (2016).
Kopec, A. et al., "Fibrin(ogen) drives repair after acetaminophen-induced liver injury via leukocyte alphaMbeta2 integrin-dependent upregulation of MMP12," J Hepatol., vol. 66(4): 787-797 (2017).
Luyendyk, J. et al., "Fibrinogen Deficiency Increases Liver Injury and Early Growth Response-1 (EGR-1) Expression in a Model of Chronic Xenobiotic-Induced Cholestasis," Gastrointestinal, Hepatobiliary, and Pancreatic Pathology, The American Journal of Pathology, vol. 178(3):1117-11125 (2011).
McWilliam, L.J., "Drug-induced renal disease," Current Diagnostic Pathology, vol. 13(1): 25-31 (2007).
Neubauer, K. et al., "Accumulation and cellular localization of fibrinogen/fibrin during short-term and long-term rat liver injury" Gastroenterology, vol. 108(4):1124-35 (1995).
Rijken, D. et al., "Basic Principles in Thrombolysis: Regulatory Role of Plasminogen," Thrombosis Research, vol. 103:S41-S49 (2011).
Schmitz, V. et al., "Plasminogen fragment K1-5 improves survival in a murine hepatocellular carcinoma model", vol. 56:271-278(2007).
Score Search results, conducted on Jan. 15, 2020, 6 pages of PDF.
Sullivan, B. et al., "Gastrointestinal, Hepatobiliary, and Pancreatic Pathology, Fibrin(ogen) Independent Role of Plasminogen Activators in Acetaminophen-Induced Liver Injury," The American Journal of Pathology, vol. 180 (6):2321-2329 (2012).
U.S. Appl. No. 16/062,037, Sep. 3, 2020.
U.S. Appl. No. 16/062,049, Sep. 3, 2020.
U.S. Appl. No. 16/062,389, Sep. 18, 2020.
U.S. Appl. No. 16/062,410, Sep. 16, 2020.
U.S. Appl. No. 16/063,534, Aug. 18, 2020.

* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      human plasminogen(Glu-PLG,Glu-plasminogen) without the signal
      peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
```

```
acctgcaggg cattccaata tcacagtaaa gagcaacaat gtgtgataat ggctgaaaac    180
aggaagtcct ccataatcat taggatgaga gatgtagttt tatttgaaaa gaaagtgtat    240
ctctcagagt gcaagactgg gaatggaaag aactacagag ggacgatgtc caaaacaaaa    300
aatggcatca cctgtcaaaa atggagttcc acttctcccc acagacctag attctcacct    360
gctacacacc cctcagaggg actggaggag aactactgca ggaatccaga caacgatccg    420
caggggccct ggtgctatac tactgatcca gaaaagagat atgactactg cgacattctt    480
gagtgtgaag aggaatgtat gcattgcagt ggagaaaact atgacggcaa aatttccaag    540
accatgtctg gactggaatg ccaggcctgg gactctcaga gcccacacgc tcatggatac    600
attccttcca aatttccaaa caagaacctg aagaagaatt actgtcgtaa ccccgatagg    660
gagctgcggc cttggtgttt caccaccgac cccaacaagc gctgggaact tgtgacatc     720 ccccgctgca caacacctcc accatcttct ggtcccacct accagtgtct gaagggaaca    780
ggtgaaaact atcgcgggaa tgtggctgtt accgtgtccg gcacacctg tcagcactgg     840 agtgcacaga cccctcacac acataacagg acaccagaaa acttcccctg caaaaatttg    900
gatgaaaact actgccgcaa tcctgacgga aaaagggccc catggtgcca tacaaccaac    960
agccaagtgc ggtgggagta ctgtaagata ccgtcctgtg actcctcccc agtatccacg   1020
gaacaattgg ctcccacagc accacctgag ctaaccctg tggtccagga ctgctaccat    1080
ggtgatggac agagctaccg aggcacatcc tccaccacca ccacaggaaa gaagtgtcag   1140
tcttggtcat ctatgacacc acaccggcac cagaagaccc cagaaaacta cccaaatgct   1200
ggcctgacaa tgaactactg caggaatcca gatgccgata aaggcccctg tgttttacc    1260 acagacccca cgtcaggtg ggagtactgc aacctgaaaa aatgctcagg aacagaagcg    1320
agtgttgtag cacctccgcc tgttgtcctg cttccagatg tagagactcc ttccgaagaa   1380
gactgtatgt ttgggaatgg gaaaggatac cgaggcaaga gggcgaccac tgttactggg   1440
acgccatgcc aggactgggc tgcccaggag ccccatagac acagcatttt cactccagag   1500
acaaatccac gggcgggtct ggaaaaaaat tactgccgta accctgatgg tgatgtaggt   1560
ggtccctggt gctacacgac aaatccaaga aaactttacg actactgtga tgtccctcag   1620
tgtgcggccc cttcatttga ttgtgggaag cctcaagtgg agccgaagaa atgtcctgga   1680
agggttgtag gggggtgtgt ggcccaccca cattcctggc cctggcaagt cagtcttaga   1740
acaaggtttg gaatgcactt ctgtggaggc accttgatat ccccagagtg ggtgttgact   1800
gctgcccact gcttggagaa gtccccaagg ccttcatcct acaaggtcat cctgggtgca   1860
caccaagaag tgaatctcga accgcatgtt caggaaatag aagtgtctag gctgttcttg   1920
gagcccacac gaaaagatat tgccttgcta aagctaagca gtcctgccgt catcactgac   1980
aaagtaatcc cagcttgtct gccatcccca aattatgtgg tcgctgaccg gaccgaatgt   2040
ttcatcactg gctggggaga aacccaaggt actttggag ctggccttct caaggaagcc    2100
cagctccctg tgattgagaa taaagtgtgc aatcgctatg agtttctgaa tggaagagtc   2160
caatccaccg aactctgtgc tgggcatttg gccggaggca ctgacagttg ccagggtgac   2220
agtggaggtc ctctggtttg cttcgagaag gacaaataca ttttacaagg agtcacttct   2280
tggggtcttg gctgtgcacg ccccaataag cctggtgtct atgttcgtgt ttcaaggttt   2340
gttacttgga ttgagggagt gatgagaaat aattaa                              2376
```

<210> SEQ ID NO 2

```
<211> LENGTH: 791
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the natural human
      plasminogen(Glu-PLG,Glu-plasminogen)without the
      signal peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350
```

```
Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
            450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
            675                 680                 685

Gln Gly Thr Phe Gly Ala Gly Leu Leu Lys Glu Ala Gln Leu Pro Val
            690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
            725                 730                 735

Cys Gln Gly Asp Ser Gly Gly Pro Leu Val Cys Phe Glu Lys Asp Lys
                740                 745                 750

Tyr Ile Leu Gln Gly Val Thr Ser Trp Gly Leu Gly Cys Ala Arg Pro
            755                 760                 765

Asn Lys Pro Gly Val Tyr Val Arg Val Ser Arg Phe Val Thr Trp Ile
```

Glu Gly Val Met Arg Asn Asn
785                 790

<210> SEQ ID NO 3
<211> LENGTH: 2433
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      plasminogen (from swiss prot)with the signal peptide

<400> SEQUENCE: 3

| | | | | |
|---|---|---|---|---|
| atggaacata | aggaagtggt | tcttctactt | cttttatttc | tgaaatcagg tcaaggagag | 60 |
| cctctggatg | actatgtgaa | tacccagggg | gcttcactgt | tcagtgtcac taagaagcag | 120 |
| ctgggagcag | gaagtataga | agaatgtgca | gcaaaatgtg | aggaggacga agaattcacc | 180 |
| tgcagggcat | tccaatatca | cagtaaagag | caacaatgtg | tgataatggc tgaaaacagg | 240 |
| aagtcctcca | taatcattag | gatgagagat | gtagttttat | ttgaaaagaa agtgtatctc | 300 |
| tcagagtgca | agactgggaa | tggaaagaac | tacagaggga | cgatgtccaa aacaaaaaat | 360 |
| ggcatcacct | gtcaaaaatg | gagttccact | tctccccaca | gacctagatt ctcacctgct | 420 |
| acacacccct | cagagggact | ggaggagaac | tactgcagga | atccagacaa cgatccgcag | 480 |
| gggcgctggt | gctatactac | tgatccagaa | aagagatatg | actactgcga cattcttgag | 540 |
| tgtgaagagg | aatgtatgca | ttgcagtgga | gaaaactatg | acggcaaaat ttccaagacc | 600 |
| atgtctggac | tggaatgcca | ggcctggac | tctcagagcc | cacacgctca tggatacatt | 660 |
| ccttccaaat | ttccaaacaa | gaacctgaag | aagaattact | gtcgtaaccc cgataggag | 720 |
| ctgcggcctt | ggtgtttcac | caccgacccc | aacaagcgct | gggaactttg tgacatcccc | 780 |
| cgctgcacaa | cacctccacc | atcttctggt | cccacctacc | agtgtctgaa gggaacaggt | 840 |
| gaaaactatc | gcgggaatgt | ggctgttacc | gtgtccgggc | acacctgtca gcactggagt | 900 |
| gcacagaccc | ctcacacaca | taacaggaca | ccagaaaact | tcccctgcaa aaatttggat | 960 |
| gaaaactact | gccgcaatcc | tgacggaaaa | agggccccat | ggtgccatac aaccaacagc | 1020 |
| caagtgcggt | gggagtactg | taagataccg | tcctgtgact | cctccccagt atccactgaa | 1080 |
| caattggctc | ccacagcacc | acctgagcta | acccctgtgg | tccaggactg ctaccatggt | 1140 |
| gatggacaga | gctaccgagg | cacatcctcc | accaccacca | gaaaagaa gtgtcagtct | 1200 |
| tggtcatcta | tgacaccaca | ccggcaccag | aagacccag | aaaactaccc aaatgctggc | 1260 |
| ctgacaatga | actactgcag | gaatccagat | gccgataaag | gccctggtg ttttaccaca | 1320 |
| gaccccagcg | tcaggtggga | gtactgcaac | ctgaaaaat | gctcaggaac agaagcgagt | 1380 |
| gttgtagcac | ctccgcctgt | tgtcctgctt | ccagatgtag | agactccttc gaagaagac | 1440 |
| tgtatgtttg | gaatgggaa | aggataccga | ggcaagaggg | cgaccactgt tactgggacg | 1500 |
| ccatgccagg | actgggctgc | ccaggagccc | catagacaca | gcatttttcac tccagagaca | 1560 |
| aatccacggg | cgggtctgga | aaaaaattac | tgccgtaacc | ctgatggtga tgtaggtggt | 1620 |
| ccctggtgct | acacgacaaa | tccaagaaaa | ctttacgact | actgtgatgt ccctcagtgt | 1680 |
| gcggccctt | catttgattg | tgggaagcct | caagtggagc | gaagaaatg tcctggaagg | 1740 |
| gttgtagggg | ggtgtgtggc | ccacccacat | tcctggccct | ggcaagtcag tcttagaaca | 1800 |

-continued

```
aggtttggaa tgcacttctg tggaggcacc ttgatatccc cagagtgggt gttgactgct   1860
gcccactgct tggagaagtc cccaaggcct tcatcctaca aggtcatcct gggtgcacac   1920
caagaagtga atctcgaacc gcatgttcag gaaatagaag tgtctaggct gttcttggag   1980
cccacacgaa aagatattgc cttgctaaag ctaagcagtc ctgccgtcat cactgacaaa   2040
gtaatcccag cttgtctgcc atccccaaat tatgtggtcg ctgaccggac cgaatgtttc   2100
atcactggct ggggagaaac ccaaggtact tttggagctg ccttctcaa ggaagcccag    2160 ctccctgtga ttgagaataa agtgtgcaat cgctatgagt ttctgaatgg aagagtccaa   2220
tccaccgaac tctgtgctgg catttggcc ggaggcactg acagttgcca gggtgacagt    2280
ggaggtcctc tggtttgctt cgagaaggac aaatacattt tacaaggagt cacttcttgg   2340
ggtcttggct gtgcacgccc caataagcct ggtgtctatg ttcgtgtttc aaggtttgtt   2400
acttggattg agggagtgat gagaaataat taa                                2433
```

<210> SEQ ID NO 4
<211> LENGTH: 810
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Amino acid sequence coding for the natural
plasminogen (from swiss prot)with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
```

```
           225                 230                 235                 240
Leu Arg Pro Trp Cys Phe Thr Thr Asp Pro Asn Lys Arg Trp Glu Leu
                    245                 250                 255

Cys Asp Ile Pro Arg Cys Thr Thr Pro Pro Ser Ser Gly Pro Thr
                260                 265                 270

Tyr Gln Cys Leu Lys Gly Thr Gly Glu Asn Tyr Arg Gly Asn Val Ala
            275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
                340                 345                 350

Asp Ser Ser Pro Val Ser Thr Glu Gln Leu Ala Pro Thr Ala Pro Pro
            355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
    435                 440                 445

Cys Asn Leu Lys Lys Cys Ser Gly Thr Glu Ala Ser Val Val Ala Pro
                450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
    515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
    595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655
```

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for LYS77-PLG(Lys-
      plasminogen)

<400> SEQUENCE: 5
aaagtgtatc tctcagagtg caagactggg aatggaaaga actacagagg gacgatgtcc      60
aaaacaaaaa atggcatcac ctgtcaaaaa tggagttcca cttctcccca cagacctaga    120
ttctcacctg ctacacaccc ctcagaggga ctggaggaga actactgcag gaatccagac    180
aacgatccgc aggggccctg tgctatact actgatccag aaaagagata tgactactgc    240
gacattcttg agtgtgaaga ggaatgtatg cattgcagtg gagaaaacta tgacggcaaa    300
atttccaaga ccatgtctgg actggaatgc caggcctggg actctcagag cccacacgct    360
catggataca ttccttccaa atttccaaac aagaacctga agaagaatta ctgtcgtaac    420 cccgatagg agctgcggcc ttggtgtttc accaccgacc caacaagcg ctgggaactt    480 tgtgacatcc ccgctgcac aacacctcca ccatcttctg gtcccaccta ccagtgtctg    540
aagggaacag gtgaaaacta tcgcgggaat gtggctgtta ccgtgtccgg gcacacctgt    600
cagcactgga gtgcacagac ccctcacaca cataacagga caccagaaaa cttcccctgc    660
aaaaatttgg atgaaaacta ctgccgcaat cctgacggaa aagggccccc atggtgccat    720
acaaccaaca gccaagtgcg gtgggagtac tgtaagatac cgtcctgtga ctcctcccca    780
gtatccacgg aacaattggc tcccacagca ccacctgagc taacccctgt ggtccaggac    840
tgctaccatg gtgatggaca gagctaccga ggcacatcct ccaccaccac cacaggaaag    900
aagtgtcagt cttggtcatc tatgacacca caccggcacc agaagacccc agaaaactac    960
ccaaatgctg gcctgacaat gaactactgc aggaatccag atgccgataa aggcccctgg   1020

```
tgttttacca cagaccccag cgtcaggtgg gagtactgca acctgaaaaa atgctcagga    1080
acagaagcga gtgttgtagc acctccgcct gttgtcctgc ttccagatgt agagactcct    1140
tccgaagaag actgtatgtt tgggaatggg aaaggatacc gaggcaagag ggcgaccact    1200
gttactggga cgccatgcca ggactgggct gcccaggagc cccatagaca cagcattttc    1260
actccagaga caaatccacg ggcgggtctg gaaaaaaatt actgccgtaa ccctgatggt    1320
gatgtaggtg gtccctggtg ctacacgaca aatccaagaa aactttacga ctactgtgat    1380
gtccctcagt gtgcggcccc ttcatttgat tgtgggaagc tcaagtggaa gccgaagaaa    1440
tgtcctggaa gggttgtagg ggggtgtgtg cccacccac attcctggcc ctggcaagtc     1500
agtcttagaa caaggtttgg aatgcacttc tgtggaggca ccttgatatc cccagagtgg    1560
gtgttgactg ctgcccactg cttggagaag tccccaaggc cttcatccta caaggtcatc    1620
ctgggtgcac accaagaagt gaatctcgaa ccgcatgttc aggaaataga agtgtctagg    1680
ctgttcttgg agcccacacg aaaagatatt gccttgctaa agctaagcag tcctgccgtc    1740
atcactgaca aagtaatccc agcttgtctg ccatccccaa attatgtggt cgctgaccgg    1800
accgaatgtt tcatcactgg ctggggagaa cccaaggta cttttggagc tggccttctc     1860
aaggaagccc agctccctgt gattgagaat aaagtgtgca atcgctatga gtttctgaat    1920
ggaagagtcc aatccaccga actctgtgct gggcatttgg ccggaggcac tgacagttgc    1980
cagggtgaca gtggaggtcc tctggtttgc ttcgagaagg acaaatacat tttacaagga    2040
gtcacttctt ggggtcttgg ctgtgcacgc cccaataagc tggtgtctta tgttcgtgtt    2100
tcaaggtttg ttacttggat tgagggagtg atgagaaata attaa                   2145
```

<210> SEQ ID NO 6
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of LYS77-PLG(Lys-
      plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140
```

```
Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
            165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
            245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
            325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
        370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
            405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
            435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
            485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
```

```
                   565                 570                 575
        Ser Pro Ala Val Ile Thr Asp Lys Val Ile Pro Ala Cys Leu Pro Ser
                    580                 585                 590

Pro Asn Tyr Val Val Ala Asp Arg Thr Glu Cys Phe Ile Thr Gly Trp
                    595                 600                 605

Gly Glu Thr Gln Gly Thr Phe Gly Ala Gly Leu Leu Lys Glu Ala Gln
                    610                 615                 620

Leu Pro Val Ile Glu Asn Lys Val Cys Asn Arg Tyr Glu Phe Leu Asn
        625                 630                 635                 640

Gly Arg Val Gln Ser Thr Glu Leu Cys Ala Gly His Leu Ala Gly Gly
                            645                 650                 655

Thr Asp Ser Cys Gln Gly Asp Ser Gly Gly Pro Leu Val Cys Phe Glu
                    660                 665                 670

Lys Asp Lys Tyr Ile Leu Gln Gly Val Thr Ser Trp Gly Leu Gly Cys
                    675                 680                 685

Ala Arg Pro Asn Lys Pro Gly Val Tyr Val Arg Val Ser Arg Phe Val
                    690                 695                 700

Thr Trp Ile Glu Gly Val Met Arg Asn Asn
        705                 710

<210> SEQ ID NO 7
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for delta-plg(delta-
      plasminogen)

<400> SEQUENCE: 7
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc aaaacaaaa      300 aatggcatca cctgtcaaaa atggagttcc acttctcccc acagacctag attctcacct     360
gctacacacc cctcagaggg actggaggag aactactgca ggaatccaga caacgatccg     420 caggggcct ggtgctatac tactgatcca gaaaagagat atgactactg cgacattctt     480
gagtgtgaag aggcggcccc ttcatttgat tgtgggaagc ctcaagtgga gccgaagaaa    540
tgtcctggaa gggttgtagg ggggtgtgtg gcccacccac attcctggcc ctggcaagtc    600
agtcttagaa caaggtttgg aatgcacttc tgtggaggca ccttgatatc cccagagtgg    660
gtgttgactg ctgcccactg cttggagaag tccccaaggc cttcatccta caaggtcatc    720
ctgggtgcac accaagaagt gaatctcgaa ccgcatgttc aggaaataga agtgtctagg    780
ctgttcttgg agcccacacg aaaagatatt gccttgctaa agctaagcag tcctgccgtc    840
atcactgaca aagtaatccc agcttgtctg ccatccccaa attatgtggt cgctgaccgg    900
accgaatgtt tcatcactgg ctggggagaa acccaaggta cttttggagc tggccttctc    960
aaggaagccc agctccctgt gattgagaat aaagtgtgca atcgctatga gtttctgaat   1020
ggaagagtcc aatccaccga actctgtgct gggcatttgg ccggaggcac tgacagttgc   1080
```

-continued

```
cagggtgaca gtggaggtcc tctggtttgc ttcgagaagg acaaatacat tttacaagga    1140
gtcacttctt gggtcttggc ctgtgcacgc cccaataagc ctggtgtcta tgttcgtgtt    1200
tcaaggtttg ttacttggat tgagggagtg atgagaaata attaa                    1245
```

<210> SEQ ID NO 8
<211> LENGTH: 414
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Amino acid sequence of delta-plg(delta-
     plasminogen)

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320
```

Lys Glu Ala Gln Leu Pro Val Ile Glu Asn Lys Val Cys Asn Arg Tyr
              325                 330                 335

Glu Phe Leu Asn Gly Arg Val Gln Ser Thr Glu Leu Cys Ala Gly His
              340                 345                 350

Leu Ala Gly Gly Thr Asp Ser Cys Gln Gly Asp Ser Gly Gly Pro Leu
              355                 360                 365

Val Cys Phe Glu Lys Asp Lys Tyr Ile Leu Gln Gly Val Thr Ser Trp
              370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
              405                 410

<210> SEQ ID NO 9
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for Mini-plg(mini-
      plasminogen)

<400> SEQUENCE: 9
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aggataccg aggcaagagg gcgaccactg ttactgggac gccatgccag      180
gactgggctg cccaggagcc ccatagacac agcattttca ctccagagac aaatccacgg     240
gcgggtctgg aaaaaaatta ctgccgtaac cctgatggtg atgtaggtgg tccctggtgc     300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt ccccaaggcc ttcatcctac aaggtcatcc tgggtgcaca ccaagaagtg     600
aatctcgaac gcatgttca ggaaatagaa gtgtctaggc tgttcttgga gcccacacga      660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca aggaagccca gctccctgtg     840
attgagaata agtgtgcaa tcgctatgag tttctgaatg gaagagtcca atccaccgaa      900
ctctgtgctg gcatttggc cggaggcact gacagttgcc agggtgacag tggaggtcct     960
ctggtttgct cgagaagga caaatacatt ttacaaggag tcacttcttg ggtcttggc     1020 tgtgcacgcc ccaataagcc tggtgtctat gttcgtgttt caaggtttgt tacttggatt    1080
gagggagtga tgagaaataa ttaa                                            1104

<210> SEQ ID NO 10
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: Amino acid sequence of Mini-plg(mini-plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
                20              25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
                100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
                180                 185                 190

Ile Leu Gly Ala His Gln Glu Val Asn Leu Glu Pro His Val Gln Glu
            195                 200                 205

Ile Glu Val Ser Arg Leu Phe Leu Glu Pro Thr Arg Lys Asp Ile Ala
            210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
            275                 280                 285

Tyr Glu Phe Leu Asn Gly Arg Val Gln Ser Thr Glu Leu Cys Ala Gly
            290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
                340                 345                 350

Val Ser Arg Phe Val Thr Trp Ile Glu Gly Val Met Arg Asn Asn
                355                 360                 365
```

<210> SEQ ID NO 11
<211> LENGTH: 750
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotide sequence coding for Micro-plg(micro-plasminogen)

<400> SEQUENCE: 11

```
gccccttcat tgattgtgg gaagcctcaa gtggagccga agaaatgtcc tggaagggtt      60
gtaggggggt gtgtggccca cccacattcc tggccctggc aagtcagtct tagaacaagg    120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga aaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                    750
```

<210> SEQ ID NO 12
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence coding for Micro-plg(micro-plasminogen)

<400> SEQUENCE: 12

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160
```

Pro Val Ile Glu Asn Lys Val Cys Asn Arg Tyr Glu Phe Leu Asn Gly
               165               170               175

Arg Val Gln Ser Thr Glu Leu Cys Ala Gly His Leu Ala Gly Gly Thr
         180               185               190

Asp Ser Cys Gln Gly Asp Ser Gly Pro Leu Val Cys Phe Glu Lys
         195               200               205

Asp Lys Tyr Ile Leu Gln Gly Val Thr Ser Trp Gly Leu Gly Cys Ala
210               215               220

Arg Pro Asn Lys Pro Gly Val Tyr Val Arg Val Ser Arg Phe Val Thr
225               230               235               240

Trp Ile Glu Gly Val Met Arg Asn Asn
         245

<210> SEQ ID NO 13
<211> LENGTH: 684
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Nucleotide sequence coding for the serine
    protease domain

<400> SEQUENCE: 13

```
gttgtagggg ggtgtgtggc ccacccacat tcctggccct ggcaagtcag tcttagaaca      60
aggtttggaa tgcacttctg tggaggcacc ttgatatccc cagagtgggt gttgactgct     120
gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg catttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                           684
```

<210> SEQ ID NO 14
<211> LENGTH: 228
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Amino acid sequence coding for the serine
    protease domain

<400> SEQUENCE: 14

Val Val Gly Gly Cys Val Ala His Pro His Ser Trp Pro Trp Gln Val
1               5               10               15

Ser Leu Arg Thr Arg Phe Gly Met His Phe Cys Gly Gly Thr Leu Ile
         20               25               30

Ser Pro Glu Trp Val Leu Thr Ala Ala His Cys Leu Glu Lys Ser Pro
               35               40               45

```
-continued

Arg Pro Ser Ser Tyr Lys Val Ile Leu Gly Ala His Gln Glu Val Asn
    50              55                  60

Leu Glu Pro His Val Gln Glu Ile Glu Val Ser Arg Leu Phe Leu Glu
65              70                  75                      80

Pro Thr Arg Lys Asp Ile Ala Leu Leu Lys Leu Ser Ser Pro Ala Val
            85                  90              95

Ile Thr Asp Lys Val Ile Pro Ala Cys Leu Pro Ser Pro Asn Tyr Val
            100             105             110

Val Ala Asp Arg Thr Glu Cys Phe Ile Thr Gly Trp Gly Glu Thr Gln
        115             120             125

Gly Thr Phe Gly Ala Gly Leu Leu Lys Glu Ala Gln Leu Pro Val Ile
        130             135             140

Glu Asn Lys Val Cys Asn Arg Tyr Glu Phe Leu Asn Gly Arg Val Gln
145             150             155                         160

Ser Thr Glu Leu Cys Ala Gly His Leu Ala Gly Gly Thr Asp Ser Cys
                165             170             175

Gln Gly Asp Ser Gly Gly Pro Leu Val Cys Phe Glu Lys Asp Lys Tyr
            180             185             190

Ile Leu Gln Gly Val Thr Ser Trp Gly Leu Gly Cys Ala Arg Pro Asn
        195             200             205

Lys Pro Gly Val Tyr Val Arg Val Ser Arg Phe Val Thr Trp Ile Glu
    210             215             220

Gly Val Met Arg
225
```

METHOD FOR PREVENTING OR TREATING RADIATION AND CHEMICAL DAMAGE

CROSS-REFERENCE TO RELATED APPLICATIONS

This application is a 35 U.S.C. 371 national stage filing of International Application No. PCT/CN2016/110455, filed on Dec. 16, 2016, which claims priority to International Application No. PCT/CN2015/097949, filed on Dec. 18, 2015. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 19, 2018, is named BCLS-003US_Sequence-2.txt and is 48,339 bytes in size.

FIELD OF THE INVENTION

The present invention relates to use of plasminogen or plasmin in prevention and/or treatment, amelioration and/or elimination of radiation and chemical damage and related diseases in a subject, and further provides a novel prevention and/or therapeutic strategy for preventing and/or treating different types of radiation and chemical damage.

BACKGROUND OF THE INVENTION

Radiation damage is damage to body tissue caused by radioactive rays exposure. Generally speaking, radioactive rays are high-energy electromagnetic waves or high-energy particles generated by natural or artificial energy sources. Instant exposure to high-dose radiation or long-term exposure to low-dose radiation may cause tissue damage. Chemical damage is local or systemic damage that occurs when chemicals contact human body. The degree of damage is related to the property of the chemicals, dosage, concentration, contact time and area, whether the treatment is timely and effective, and other factors. Clinically, radiotherapy or chemotherapy or a combination of the two is commonly used for treating or ameliorating tumor and cancer patients. Radiotherapy usually uses X-rays, gamma rays, neutrons and radiation from other sources to kill cancer cells or destroy genetic material within cells. Chemotherapy destroys cancer cell replication or proliferation by using cytotoxic drug alone or in combination. Almost all cancer patients exhibit severe side effects after going through one or more radiotherapy, chemotherapy or chemoradiotherapy, including mucosal ulcers, decreased immune function, bone marrow suppression, digestive disorders, inflammation, cardiotoxicity, nephrotoxicity, pulmonary fibrosis, phlebitis, neurotoxicity, hepatotoxicity, etc. . . . . Therefore, the prevention of the side effects of chemotherapy and radiotherapy and protection are crucial for cancer patients.

Plasmin is a key component of the plasminogen activation system (PA system). It is a broad-spectrum protease which can hydrolyze several components of the extracellular matrix (ECM), including fibrin, gelatin, fibronectin, laminin and proteoglycans[1]. In addition, plasmin can activate some pro-metalloproteinases (pro-MMP) to form active metalloproteinases (MMP). Therefore, plasmin is considered to be an important upstream regulator of extracellular proteolysis[2, 3]. Plasmin is formed by proteolysis of plasminogen by two physiological PAs: tissue plasminogen activator (tPA) or urokinase-type plasminogen activator (uPA). Due to the relatively high level of plasminogen in plasma and other body fluids, it is conventionally believed that the regulation of the PA system is primarily achieved through PA synthesis and the level of activity. The synthesis of PA system components is strictly regulated by different factors such as hormones, growth factors and cytokines. In addition, there are also specific physiological inhibitors of plasmin and PA. The major inhibitor of plasmin is α2-antiplasmin. Some cells have on surfaces a direct hydrolytically active uPA specific cell surface receptor (uPAR)[4, 5].

Plasminogen (plg) is a single-stranded glycoprotein composed of 791 amino acids and has a molecular weight of approximately 92 kDa[6,7]. Plasminogen is mainly synthesized in the liver and is abundantly present in the extracellular fluid. The amount of plasminogen in plasma is approximately 2 μM. Therefore, plasminogen is a huge potential source of proteolytic activity in tissues and body fluids[8, 9]. Plasminogen has two molecular forms: glu-plasminogen and lys-plasminogen. Plasminogen of naturally secreted and uncleaved forms has an amino-terminal (N-terminal) glutamic acid, and thus it is referred to as glutamate-plasminogen. However, when plasmin is present, glutamate-plasminogen is hydrolyzed to lysine-plasminogen at Lys 76-Lys 77. Comparing with glutamate-plasminogen, lysine-plasminogen has a higher affinity for fibrin and can be activated by PA at a higher rate. The Arg 560-Val 561 peptide bonds of these two forms of plasminogen can be cleaved by uPA or tPA, leading to the formation of disulfide-linked double-stranded protease plasmin[10]. The amino-terminal portion of plasminogen contains five homotrimeric rings, i.e., the so-called kringles, and the carboxy-terminal portion contains a protease domain. Some kringles contain lysine bonding sites that mediate the specific interaction of plasminogen with fibrin and its inhibitor α2-AP. It has been recently discovered a fragment of plasminogen of 38 kDa, including kringle 1-4, which is an effective inhibitor of angiogenesis. This fragment is named angiosatin and can be produced by proteolysis of plasminogen by several proteases.

The main substrate of plasmin is fibrin, and fibrinolysis is the key to prevent phathological thrombosis[11]. Plasmin also has substrate specificity for several components of ECM, including laminin, fibronectin, proteoglycans, and gelatin, which indicates that plasmin also plays an important role in ECM remodeling[7, 12, 13]. Indirectly, plasmin can also degrade other components of ECM by converting certain protease precursors into active proteases, including MMP-1, MMP-2, MMP-3 and MMP-9. Therefore, it has been suggested that plasmin may be an important upstream regulator of extracellular proteolysis[14]. In addition, plasmin has the ability to activate certain potential forms of growth factors[15-17]. In vitro, plasmin can also hydrolyze components of the complement system and release chemotactic complement fragments.

We have surprisingly found in our research that plasminogen or plasmin has a significant therapeutic effect on radiation and chemical damage to the body and is of high safety. Therefore, the use of plasminogen or plasmin is a novel therapeutic strategy for the treatment of different types of radiation and chemical damage and related diseases.

SUMMARY OF THE INVENTION

In one aspect, the present invention relates to the use of plasminogen or plasmin in the preparation of a drug for treating and/or eliminating radiation damage and chemical damage and related diseases in a subject. The present invention also relates to the use of plasminogen or plasmin in the preparation of a drug for treating and/or eliminating body organ and tissue damage and related diseases caused by radiotherapy, chemotherapy or chemoradiotherapy in a subject. In one embodiment, the damage includes damage to a bone marrow hematopoietic system, skin, mucous membrane, an immune system and a reproductive system. In one embodiment, the damage includes damage to a liver, spleen, kidney, lung, gastrointestinal tract, thymus, bone marrow, testis and epididymis. In one embodiment, the damage is a decrease in general healthy conditions, systemic side effects and local side effects including acute side effects, long-term side effects and cumulative side effects caused by radiotherapy, chemotherapy or chemoradiotherapy. In one embodiment, the damage-related diseases include mucosal ulcers, decreased immune function, myelosuppression, digestive dysfunction, heart, liver, spleen, lung, kidney, ovarian, testicular toxicity dysfunctions, and neurotoxicity dysfunction. In one embodiment, the plasminogen has a sequence identity of at least 80%, 85%, 90%, 95%, 96%, 97%, 98% or 99% with SEQ ID NO: 2, 6, 8, 10 or 12 and still has plasminogen activity. In one embodiment, the plasminogen is a protein including a plasminogen active fragment and still having plasminogen activity. In one embodiment, the plasminogen or plasmin is administered in combination with one or more other drugs or therapies, including anti-cancer drugs, anti-infective drugs, immunopotentiators, analgesics, nutrients and antidotes.

In one embodiment, the subject is a mammal, preferably a human.

In one embodiment, the subject lacks plasmin or plasminogen. Specifically, the lack is congenital, secondary and/or local.

In one embodiment, the plasminogen has a sequence identity of at least 80%, 85%, 90%, 95%, 96%, 97%, 98% or 99% with SEQ ID NO: 2, 6, 8, 10 or 12 and still has plasminogen activity. In one embodiment, the plasminogen is a protein in which, based on SEQ ID NO: 2, 6, 8, 10 or 12, 1 to 100, 1 to 90, 1 to 80, 1 to 70, 1 to 60, 1 to 50, 1 to 45, 1 to 40, 1 to 35, 1 to 30, 1 to 25, 1 to 20, 1 to 15, 1 to 10, 1 to 5, 1 to 4, 1 to 3, 1 to 2, 1 amino acid is added, deleted and/or substituted and which still has plasminogen activity. In one embodiment, the plasminogen is selected from a group consisting of glu-plasminogen, lys-plasminogen, mini-plasminogen, micro-plasminogen, and δ-plasminogen, or any combination thereof. In one embodiment, the plasminogen is a conservatively substituted variant selected from variants of glu-plasminogen, lys-plasminogen, mini-plasminogen, δ-plasminogen and micro-plasminogen. In one embodiment, the plasminogen is a natural human plasminogen, such as plasminogen orthologs represented by SEQ ID NO: 2, for example, plasminogen orthologs from primates or rodents such as plasminogen orthologs from gorillas, rhesus monkeys, rats, cattle, horses and canines. Most preferably the amino acid sequence of the plasminogen of the present invention is as shown in SEQ ID NO: 2, 6, 8, 10 or 12.

In one embodiment, the plasminogen or plasmin is administered by external, oral, systemic or topical administration. In one embodiment, the administration is via surface, intravenous, intramuscular, subcutaneous, inhalation, intraspinal, local injection, intra-articular injection or through the rectum. In one embodiment, the administration is external. In one embodiment, the topical administration is administering plasminogen or plasmin directly at the damaged area for prevention and/or treatment.

In one embodiment, the plasminogen is administered in combination with a suitable polypeptide or stabilizer. In one embodiment, the plasminogen is administered in a dosage of 0.0001 to 2000 mg/kg, 0.001 to 800 mg/kg, 0.01 to 600 mg/kg, 0.1 to 400 mg/kg, 1 to 200 mg/kg, 1 to 100 mg/kg, 10 to 100 mg/kg (calculated per kilogram of body weight) or 0.0001 to 2000 mg/cm$^2$, 0.001 to 800 mg/cm$^2$, 0.01 to 600 mg/cm$^2$, 0.1 to 400 mg/cm$^2$, 1 to 200 mg/cm$^2$, 1 to 100 mg/cm$^2$, 10 to 100 mg/cm$^2$ (calculated per square centimeter of surface area) per day, preferably it is repeated at least once, and preferably administered at least daily. In the case of topical administration, the above dosage may be further adjusted depending on the circumstances.

In another aspect, the present invention relates to plasminogen or plasmin for preventing and/or treating and/or eliminating radiation damage and chemical damage and related diseases in a subject, and a pharmaceutical composition containing plasminogen or plasmin for preventing and/or treating and/or eliminating radiation damage and chemical damage and related diseases in a subject. The present invention also relates to plasminogen or plasmin for preventing and/or treating and/or eliminating body organ and tissue damage and related diseases caused by radiotherapy, chemotherapy or chemoradiotherapy in a subject, and a pharmaceutical composition containing plasminogen or plasmin for preventing and/or treating and/or eliminating body organ and tissue damage and related diseases caused by radiotherapy, chemotherapy or chemoradiotherapy in a subject. In one embodiment, the damage includes damage to a bone marrow hematopoietic system, skin, mucous membrane, an immune system and a reproductive system. In one embodiment, the damage includes damage to a liver, spleen, kidney, lung, gastrointestinal tract, thymus, bone marrow, testis and epididymis. In one embodiment, the damage is a decrease in general healthy conditions, systemic side effects and local side effects including acute side effects, long-term side effects and cumulative side effects caused by radiotherapy, chemotherapy or chemoradiotherapy. In one embodiment, the damage-related diseases include mucosal ulcers, decreased immune function, myelosuppression, digestive dysfunction, heart, liver, spleen, lung, kidney, ovarian or testicular toxicity dysfunctions, and neurotoxicity dysfunction. In one embodiment, the plasminogen has a sequence identity of at least 80%, 85%, 90%, 95%, 96%, 97%, 98% or 99% with SEQ ID NO: 2, 6, 8, 10 or 12 and still has plasminogen activity. In one embodiment, the plasminogen is a protein including a plasminogen active fragment and still having plasminogen activity. In one embodiment, the plasminogen or plasmin is administered in combination with one or more other drugs or therapies, including anti-cancer drugs, anti-infective drugs, immunopotentiators, analgesics, nutrients and antidotes.

In one embodiment, the subject is a mammal, preferably a human.

In one embodiment, the subject lacks plasmin or plasminogen. Specifically, the lack is congenital, secondary and/or local.

In one embodiment, the plasminogen has a sequence identity of at least 80%, 85%, 90%, 95%, 96%, 97%, 98% or 99% with SEQ ID NO: 2, 6, 8, 10 or 12 and still has plasminogen activity. In one embodiment, the plasminogen is a protein in which, based on SEQ ID NO: 2, 6, 8, 10 or 12, 1 to 100, 1 to 90, 1 to 80, 1 to 70, 1 to 60, 1 to 50, 1 to 45, 1 to 40, 1 to 35, 1 to 30, 1 to 25, 1 to 20, 1 to 15, 1 to 10, 1 to 5, 1 to 4, 1 to 3, 1 to 2, 1 amino acid is added, deleted and/or substituted and which still has plasminogen activity. In one embodiment, the plasminogen is selected from variants of glu-plasminogen, lys-plasminogen, mini-plasminogen, micro-plasminogen, and δ-plasminogen, or any combination thereof. In one embodiment, the plasminogen is a conservatively substituted variant selected from conservatively substituted variants of glu-plasminogen, lys-plasminogen, mini-plasminogen, δ-plasminogen and micro-plasminogen. In one embodiment, the plasminogen is a natural human plasminogen, such as plasminogen orthologs represented by SEQ ID NO: 2, for example, plasminogen orthologs from primates or rodents such as plasminogen orthologs from gorillas, rhesus monkeys, rats, cows, horses and canines. Most preferably the amino acid sequence of the plasminogen of the present invention is as shown in SEQ ID NO: 2, 6, 8, 10 or 12.

In one embodiment, the plasminogen or plasmin is administered by external, oral, systemic or topical administration. In one embodiment, the administration is via surface, intravenous, intramuscular, subcutaneous, inhalation, intraspinal, local injection, intra-articular injection or through the rectum. In one embodiment, the administration is external. In one embodiment, the topical administration is administering plasminogen or plasmin directly at the damaged area for the prevention and/or treatment.

In one embodiment, the plasminogen is administered in combination with a suitable polypeptide or stabilizer. In one embodiment, the plasminogen is administered in a dosage of 0.0001 to 2000 mg/kg, 0.001 to 800 mg/kg, 0.01 to 600 mg/kg, 0.1 to 400 mg/kg, 1 to 200 mg/kg, 1 to 100 mg/kg, 10 to 100 mg/kg (calculated per kilogram of body weight) or 0.0001 to 2000 mg/cm$^2$, 0.001 to 800 mg/cm$^2$, 0.01 to 600 mg/cm$^2$, 0.1 to 400 mg/cm$^2$, 1 to 200 mg/cm$^2$, 1 to 100 mg/cm$^2$, 10 to 100 mg/cm$^2$ (calculated per square centimeter of surface area) per day, preferably it is repeated at least once, and preferably administered at least daily. In the case of topical administration, the above dosage may be further adjusted depending on the circumstances.

In another aspect, the present invention relates to an article of manufacture or a kit containing plasminogen or plasmin for preventing and/or treating and/or eliminating radiation damage and chemical damage and related diseases in a subject, and an article of manufacture or a kit containing plasminogen or plasmin for preventing and/or treating and/or eliminating body organ and tissue damage and related diseases caused by radiotherapy, chemotherapy or chemoradiotherapy in a subject. In one embodiment, the damage includes damage to a bone marrow hematopoietic system, skin, mucous membrane, an immune system and a reproductive system. In one embodiment, the damage includes damage to a liver, spleen, kidney, lung, gastrointestinal tract, thymus, bone marrow, testis and epididymis. In one embodiment, the damage is a decrease in general healthy conditions, systemic side effects and local side effects including acute side effects, long-term side effects and cumulative side effects caused by radiotherapy, chemotherapy or chemoradiotherapy. In one embodiment, the damage-related diseases include mucosal ulcers, decreased immune function, myelosuppression, digestive dysfunction, heart, liver, spleen, lung, kidney, ovarian, testicular toxicity dysfunctions, and neurotoxicity dysfunction. In one embodiment, the plasminogen has a sequence identity of at least 80%, 85%, 90%, 95%, 96%, 97%, 98% or 99% with SEQ ID NO: 2, 6, 8, 10 or 12 and still has plasminogen activity. In one embodiment, the plasminogen is a protein including a plasminogen active fragment and still having plasminogen activity. In one embodiment, the plasminogen or plasmin is administered in combination with one or more other drugs or therapies, including anti-cancer drugs, anti-infective drugs, immunopotentiators, analgesics, nutrients and antidotes.

In one embodiment, the article or kit further comprises a container containing one or more other drugs. The kit may also include an instruction further which states that the plasminogen or plasmin can be used for preventing and/or treating the damage and related diseases, and may further state that the plasminogen or plasmin is administered before, simultaneously with, and/or after the administration of other drugs or therapies.

In one embodiment, the subject is a mammal, preferably a human.

In one embodiment, the subject lacks plasmin or plasminogen. Specifically, the lack is congenital, secondary and/or local.

In one embodiment, the plasminogen has a sequence identity of at least 80%, 85%, 90%, 95%, 96%, 97%, 98% or 99% with SEQ ID NO: 2, 6, 8, 10 or 12 and still has plasminogen activity. In one embodiment, the plasminogen is a protein in which, based on SEQ ID NO: 2, 6, 8, 10 or 12, 1 to 100, 1 to 90, 1 to 80, 1 to 70, 1 to 60, 1 to 50, 1 to 45, 1 to 40, 1 to 35, 1 to 30, 1 to 25, 1 to 20, 1 to 15, 1 to 10, 1 to 5, 1 to 4, 1 to 3, 1 to 2, 1 amino acid is added, deleted and/or substituted and which still has plasminogen activity. In one embodiment, the plasminogen is selected from a group consisting of glu-plasminogen, lys-plasminogen, mini-plasminogen, micro-plasminogen, and δ-plasminogen, or any combination thereof. In one embodiment, the plasminogen is a conservatively substituted variant selected from variants of glu-plasminogen, lys-plasminogen, mini-plasminogen, δ-plasminogen and micro-plasminogen. In one embodiment, the plasminogen is a natural human plasminogen, such as plasminogen orthologs represented by SEQ ID NO: 2, for example, plasminogen orthologs from primates or rodents such as plasminogen orthologs from gorillas, rhesus monkeys, rats, cows, horses and canines. Most preferably the amino acid sequence of the plasminogen of the present invention is as shown in SEQ ID NO: 2, 6, 8, 10 or 12.

In one embodiment, the plasminogen or plasmin is administered by external, oral, systemic or topical administration. In one embodiment, the administration is via surface, intravenous, intramuscular, subcutaneous, inhalation, intraspinal, local injection, intra-articular injection or through the rectum. In one embodiment, the administration is external. In one embodiment, the topical administration is administering plasminogen or plasmin directly at the damaged area for the prevention and/or treatment.

In one embodiment, the plasminogen is administered in combination with a suitable polypeptide or stabilizer. In one embodiment, the plasminogen is administered in a dosage of 0.0001 to 2000 mg/kg, 0.001 to 800 mg/kg, 0.01 to 600 mg/kg, 0.1 to 400 mg/kg, 1 to 200 mg/kg, 1 to 100 mg/kg, 10 to 100 mg/kg (calculated per kilogram of body weight) or 0.0001 to 2000 mg/cm$^2$, 0.001 to 800 mg/cm$^2$, 0.01 to 600 mg/cm$^2$, 0.1 to 400 mg/cm$^2$, 1 to 200 mg/cm$^2$, 1 to 100 mg/cm$^2$, 10 to 100 mg/cm$^2$ (calculated per square centimeter of surface area) per day, preferably it is repeated at least once, and preferably administered at least daily. In the case of topical administration, the above dosage may be further adjusted depending on the circumstances.

The present invention explicitly covers all combinations of technical features pertaining to embodiments of the present invention, and these combined technical solutions have been explicitly disclosed in the present application, just as that the above technical solutions have been independently and explicitly disclosed. In addition, the present invention also explicitly covers all sub-combinations of all embodiments and elements thereof, and is disclosed herein, just as that each of such sub-combinations is independently and explicitly disclosed herein.

DETAILED DESCRIPTION OF THE INVENTION

"Radiation damage", also referred to as "radiation injury", is damage (injury) to whole body or local organs or tissues caused by radioactive rays exposure. Generally speaking, radioactive rays are high-energy electromagnetic waves or high-energy particles generated by natural or artificial energy sources. Instant exposure to high-dose radiation or long-term exposure to low-dose radiation may cause organ or tissue damage. "Chemical damage" is local or systemic damage (injury) that occurs when chemicals contact human body. The degree of damage is related to the property of the chemicals, dosage, concentration, contact time and area, whether the treatment is timely and effective, and other factors.

Radiation damage and chemical damage can be manifested as damage to organs, tissues and functions of the body, for example, damage to physiological structure and function of the bone marrow hematopoietic system, damage to physiological structure and function of the skin and mucous membranes, damage to physiological structure and function of the immune system, and damage to physiological structure and function of the reproductive system. In one embodiment, the damage includes damage to the physiological structure and function of a liver, spleen, kidney, lung, gastrointestinal tract, thymus, bone marrow, testis and epididymis. The damage-related diseases are manifested as damaged organ and tissue dysfunction, such as mucosal ulcers, decreased immune function, myelosuppression, digestive dysfunction, heart, liver, spleen, lung, kidney, ovarian, testicular toxicity dysfunctions, and neurotoxicity dysfunction.

"Radiation therapy" and "radiotherapy" can be used interchangeably. The treatment with chemical drugs is generally referred to as "chemotherapy" for short. "Chemoradiotherapy" refers to a combination of radiotherapy and chemotherapy. Clinically, radiotherapy or chemotherapy or a combination of the two is commonly used for treating or ameliorating tumor and cancer patients. Radiotherapy usually uses X-rays, gamma rays, neutrons and radiation from other sources to kill cancer cells or destroy genetic material within cells. Chemotherapy destroys cancer cell replication or proliferation by using cytotoxic drug alone or in combination. Normal cells are also damaged during radiotherapy and cannot repair themselves. Side effects may occur during radiotherapy, including skin irritation, hair loss in the treatment area, and bone marrow damage.

"Chemotherapy" refers to the use of cytotoxic drug alone or in combination to kill cancer cells. Similar to radiotherapy, cancer cells can be damaged and eventually die; however, healthy cells are affected during the self-repair process after chemotherapy. Cytotoxic drugs act by interfering with the differentiation and proliferation capabilities of growing cells. Therefore, in addition to cancer cells, other cells that normally differentiate and grow rapidly are also affected. For example, they may affect the hematopoietic function of the bone marrow, causing bone marrow suppression. In addition, they may affect the digestive tract, the inner walls of the oral cavity and the reproductive system cells, and affect the hair follicles, causing diarrhea, oral pain and hair loss.

"The side effects of chemoradiotherapy" refer to side effects associated with chemoradiotherapy, usually occurring at different stages, such as during the treatment (acute side effects), months or years after the treatment (long-term side effects), or after repeated treatment (accumulated side effects). The nature, severity and length of side effect depend on the organ being treated, the treatment itself (radiotype, dose, grade, combined chemotherapy) and the patient.

Most of the side effects are predictable and expectable. The side effects of radiotherapy are usually limited to a topical area of the patient where treatment is received. A goal of the modern radiotherapy method is to minimize side effects and help patients understand and manage those unavoidable side effects.

Myelosuppression is one of the many side effects of radiotherapy and chemotherapy. The result is reduced blood cell production, including red blood cells, white blood cells, and platelets. As a result, the patient is fatigued due to anaemia and becomes susceptible to infection due to leucopenia, and due to thrombocytopenia, bruises and bleeding are more likely to occur when there is a wound.

"General health condition" is a healthy standard, and it refers to that an individual can eat, talk and participate in social activities which help to satisfy basic recreation based on that the body, related tissues and organs have no active disease, discomfort and anxiety. Main signs of general health include physical health and mental health.

"Plasmin" is a very important enzyme that exists in the blood and can hydrolyze fibrin clots into fibrin degradation products and D-dimers.

"Plasminogen" is a zymogen form of plasmin. It consists of 810 amino acids calculated from the natural human plasminogen amino acid sequence (SEQ ID NO: 4) containing a signal peptide according to the sequence in Swiss prot and has a molecular weight of about 92 kD. It is a glycoprotein synthesized mainly in the liver and capable of circulating in the blood, and the cDNA sequence encoding this amino acid sequence is shown in SEQ ID NO: 3. A full-length plasminogen includes seven domains: a serine protease domain at C-terminal, a Pan Apple (Pap) domain at N-terminal, and five Kringle domains (Kringle 1 to 5). Referring to the sequence in Swiss prot, the signal peptide includes residues Met 1-Gly 19, Pap includes residues Glu 20-Val 98, Kringle 1 includes residues Cys 103-Cys 181, Kringle 2 includes residues Glu 184-Cys 262, Kringle 3 includes residues Cys 275-Cys 352, Kringle 4 includes residues Cys 377-Cys 454, and Kringle 5 includes residues Cys 481-Cys 560. According to NCBI data, the serine protease domain includes residues Val 581-Arg 804.

Glu-plasminogen is a natural full-length plasminogen consisting of 791 amino acids (not containing signal peptide of 19 amino acids), and the cDNA sequence encoding this sequence is shown in SEQ ID NO: 1, and the amino acid sequence is shown in SEQ ID NO: 2. In vivo, lys-plasminogen, which is formed by hydrolysis at the 76th to 77th amino acids of the glu-plasminogen, is also present and is shown in SEQ ID NO: 6, and the cDNA sequence encoding this amino acid sequence is shown in SEQ ID NO: 5. δ-plasminogen is a fragment of a full-length plasminogen that lacks the Kringle 2-Kringle 5 structure and contains only the Kringle 1 and serine protease domains[18, 19]. The amino acid sequence (SEQ ID NO: 8) of δ-plasminogen has been reported[19], and the cDNA sequence encoding the amino acid sequence is shown in SEQ ID NO: 7. Mini-plasminogen consists of Kringle 5 and serine protease domains. It has been reported that it includes residues Val 443-Asn 791 (taking the glu-residue of the glu-plasminogen sequence not containing signal peptide as the starting amino acid)[20]. The amino acid sequence is shown in SEQ ID NO: 10, and the cDNA sequence encoding the amino acid sequence is shown in SEQ ID NO: 9. Micro-plasminogen only includes the serine protease domain, and it has been reported that the amino acid sequence includes residues Ala 543-Asn 791 (taking the glu-residue of the glu-plasminogen sequence not containing signal peptide as the starting amino acid)[21], It has also been reported in the patent document CN 102154253A that the sequence includes residues Lys 531-Asn 791 (taking the glu-residue of the glu-plasminogen sequence not containing signal peptide as the starting amino acid), and the sequence of the present patent application refers to the Patent Literature CN 102154253A. The amino acid sequence is shown in SEQ ID NO: 12, and the cDNA sequence encoding the amino acid sequence is shown in SEQ ID NO: 11.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

In the course of circulation, plasminogen adopts a closed inactive conformation. However, when it is bound to a thrombus or cell surface, it becomes an active plasmin in an open conformation under the mediation of a plasminogen activator (PA). The active plasmin can further hydrolyze the fibrin clot to fibrin degradation products and D-dimers, and further dissolves the thrombus. The Pap domain of plasminogen contains an important determinant that maintains plasminogen in an inactive closed conformation, whereas the KR domain is capable of binding to lysine residues present on receptors and substrates. It is known that a variety of enzymes can act as plasminogen activators, including tissue plasminogen activator (tPA), urokinase-type plasminogen activator (uPA), kallikrein and coagulation factor XII (Hageman factor).

"Plasminogen active fragment" refers to an active fragment that binds to a target sequence in a substrate and exerts a proteolytic function in a plasminogen protein. The technical solution of the present invention relating to plasminogen covers a technical solution replacing plasminogen with a plasminogen active fragment. The plasminogen active fragment of the present invention is a protein comprising a serine protease domain of plasminogen. Preferably, the plasminogen active fragment of the present invention comprises SEQ ID NO: 14, or an amino acid sequence having an amino acid sequence identity of at least 80%, 90%, 95%, 96%, 97%, 98% or 99% with SEQ ID NO: 14. Therefore, plasminogen of the present invention comprises a protein comprising the plasminogen active fragment and still having plasminogen activity.

At present, methods for testing plasminogen and its activity in blood include detection of tissue plasminogen activator activity (t-PAA), detection of plasma tissue plasminogen activator antigen (t-PAAg), detection of plasma tissue plasminogen activity (plasminogen A), detection of plasma tissue plasminogen antigen (plasminogen Ag), detection of plasma tissue plasminogen activator inhibitor activity, detection of plasma tissue plasminogen activator inhibitor antigen, and detection of plasma plasmin-antiplasmin composite (PAP). The most commonly used detection method is the chromogenic substrate method. That is, streptokinase (SK) and chromogenic substrate are added to the subject plasma, the plasminogen in the subject plasma is converted to PLM under the action of SK and PLM acts on chromogenic substrate. Then a spectrophotometer is used for measurement, and the increase in absorbance is proportional to the plasminogen activity. In addition, plasminogen activity in blood can also be measured by an immunochemical method, a gel electrophoresis, immunoturbidimetry, a radioimmuno-diffusion method, etc. . . . . .

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogen derived from different species and having plasminogen activity.

A "conservative substitutional variant" refers to a change in a given amino acid residue without changing the overall conformation and function of a protein or enzyme, which includes and is not limited to substituting amino acids in the amino acid sequence of the parental protein with amino acids of similar properties (for example, acidity, basicity, hydrophobicity, etc.). Amino acids having similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different, for example, 70% to 99% similarity (identity) based on the MEGALIGH algorithm. A "conservative substitution variant" also includes a polypeptide or enzyme having 60% or more amino acid identity determined by BLAST or FASTA algorithm, preferably 75% or more, more preferably 85% or more, most preferably 90% or more, and having the same or substantially similar properties or functions as compared with natural or parental proteins or enzymes.

"Isolated" plasminogen or plasmin refers to plasminogen or plasmin protein that is isolated and/or recovered from its natural environment. In some embodiments, the plasminogen or plasmin will be purified (1) to a purity more than 90%, more than 95%, or more than 98% (by weight), for example, more than 99% (by weight), as determined by Lowry method, (2) to an extent enough to obtain at least 15 residues of N-terminal or internal amino acid sequence by using a rotating cup sequencer, or (3) to homogeneity, the homogeneity being determined by sodium dodecyl sulfate-polyacrylamide gel electrophoresis (SDS-PAGE) using Coomassie blue or silver staining under reducing or non-reducing conditions. Isolated plasminogen or plasmin also includes plasminogen or plasmin prepared from recombinant cells by bioengineering techniques and separated by at least one purification step.

The terms "polypeptide", "peptide" and "protein" are interchangeable herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including but not limited to, fusion proteins having heterologous amino acid sequences, fusions having heterologous and homologous leader sequences (with or without N-terminal methionine residues), etc. . . . .

The "percentage (%) of amino acid sequence identity" with reference to polypeptide sequence is defined as a percentage of amino acid residues in the candidate sequence that are identical to the amino acid residues with reference to polypeptide sequence after a gap is introduced as necessary to achieve maximum percentage of sequence identity and when no conservative substitution is considered as part of sequence identity. Comparisons for the purpose of determining percentage of amino acid sequence identity may be achieved in a variety of ways within the technical scope in the art, for example, using publicly available computer software such as BLAST, BLAST-2, ALIGN or Megalign (DNASTAR) software. Those skilled in the art can determine appropriate parameters for aligning sequences, including any algorithm needed to achieve maximum contrast over the full length of the sequences being compared. However, for purposes of the present invention, the percentage of amino acid sequence identity is generated using the sequence comparison computer program ALIGN-2.

In the case of comparing amino acid sequences using ALIGN-2, the percentage of amino acid sequence identity of a given amino acid sequence A relative to a given amino acid sequence B (or may be expressed as a given amino acid sequence A having or containing a percentage of amino acid sequence identity relative to, to, or with respect to a given amino acid sequence B) is calculated as follows:

Fraction $X/Y \times 100$ wherein X is a specific number of identically matched amino acid residues scored by the sequence alignment program ALIGN-2 in the A and B alignment of the program, and Y is a total number of amino acid residues in B. It should be understood that, when the length of amino acid sequence A is not equal to the length of amino acid sequence B, the percentage of amino acid sequence identity of A relative to B will not be equal to the percentage of amino acid sequence identity of B relative to A. All percentages of amino acid sequence identity used herein are obtained using ALIGN-2 computer program as described in the previous paragraph, unless specifically stated otherwise.

As used herein, the terms "treating", "treatment" and "eliminating" refer to obtaining a desired pharmacological and/or physiological effect. The effect may be complete or partial prevention of a disease or its symptoms, and/or partial or complete cure of a disease and/or its symptoms, and includes: (a) preventing the occurrence of a disease in a subject which may have the cause of the disease but not yet diagnosed as having the disease; (b) inhibiting the disease, that is, holding back its formation; and (c) alleviating the disease and/or its symptoms, that is, causing the disease and/or its symptoms to subside.

The terms "individual", "subject" and "patient" are interchangeable herein and refer to mammals, including but not limited to rats (rats, mice), non-human primates, humans, canines, cats, hoofed animals (such as horses, cattle, sheep, pigs, goats) and the like.

A "therapeutically effective amount" or an "effective amount" refers to an amount of plasminogen sufficient to achieve the prevention and/or treatment of a disease when it is administered to a mammal or other subjects to treat a disease. The "therapeutically effective amount" will vary depending on the plasminogen used, the severity of the disease and/or its symptoms of the subject to be treated and the age, weight, etc. . . . .

Preparation of Plasminogen or Plasmin of the Present Invention

Plasminogen or plasmin can be isolated and purified from nature for further therapeutic uses, and can also be synthesized by standard chemical peptide synthesis techniques. In chemical synthesis of polypeptides, polypeptides can be synthesized via a liquid or a solid phase. Solid phase polypeptide synthesis (SPPS) (in which the C-terminal amino acid of the sequence is attached to an insoluble support, followed by sequential addition of the remaining amino acids in the sequence) is a method suitable for the chemical synthesis of plasminogen or plasmin. Various forms of SPPS such as Fmoc and Boc can be used to synthesize plasminogen or plasmin. Techniques for solid phase synthesis are described in Barany and Solid-Phase Peptide Synthesis, pages 3 to 284; The Peptides: Analysis, Synthesis, Biology, Vol. 2: Special Methods in Peptide Synthesis, Part A., Merrifield et al., J. Am. Chem. Soc., 85: 2149-2156 (1963); Stewart et al., Solid Phase Peptide Synthesis, $2^{nd}$ ed. Pierce Chem. Co., Rockford, III. (1984); and Ganesan A. 2006 Mini Rev. Med Chem. 6: 3-10 and Camarero J A et al., 2005 Protein Pept Lett. 12: 723-8. In short, small insoluble porous beads are treated with a functional unit on which a peptide chain is built. After repeated cycles of coupling/deprotection, the attached solid-phase free N-terminal amine is coupled to a single N-protected amino acid unit. Then the unit is deprotected to expose new N-terminal amines that can be attached to other amino acids. The peptide remains fixed on the solid phase before it is cut off.

Standard recombinant methods can be used to produce the plasminogen of the present invention. For example, a nucleic acid encoding a plasminogen is inserted into an expression vector such that it is operably linked to a regulatory sequence in the expression vector. Expression regulatory sequences include, but are not limited to, promoters (for example, naturally associated or heterologous promoters), signal sequences, enhancer elements, and transcription termination sequences. Expression regulation can be a eukaryotic promoter system in a vector which is capable of transforming or transfecting eukaryotic host cells (for example, COS or CHO cells). Once the vector is incorporated into a suitable host, the host is maintained under conditions suitable for a high-level expression of the nucleotide sequence and collection and purification of plasminogen.

Suitable expression vectors are usually replicated in the host organism as episomes or as an integral part of the host chromosomal DNA. In general, an expression vector contains a selection marker (e.g., ampicillin resistance, hygromycin resistance, tetracycline resistance, kanamycin resistance, or neomycin resistance) to help to test cells that have been transformed with the desired DNA sequence of foreign sources.

*Escherichia coli* is an example of a prokaryotic host cell that can be used to clone the subject antibody-encoding polynucleotide. Other microbial hosts suitable for use include bacilli, such as *Bacillus subtilis* and other Enterobacteriaceae, such as *Salmonella, Serratia*, and various *Pseudomonas* species. Expression vectors can also be generated in these prokaryotic hosts and will usually contain expression regulatory sequences (e.g., origins of replication) that are compatible with the host cells. In addition, there will be many well-known promoters, such as lactose promoter system, tryptophan (trp) promoter system, β-lactamase promoter system, or promoter system from phage lambda. The promoters usually regulate expressions to initiate and complete transcription and translation optionally in a case of manipulation of gene sequences and having ribosome binding site sequences and the like.

Other microorganisms, such as yeasts, can also be used for expression. Yeast (such as *S. cerevisiae*) and *Pichia* are examples of suitable yeast host cells, where suitable vectors have expression regulatory sequences (such as promoters), origins of replication, termination sequences and the like as needed. Typical promoters include 3-phosphoglycerate kinase and other saccharolytic enzymes. Inducible yeast is initiated by promoters that specifically include enzymes derived from alcohol dehydrogenase, isocytochrome C, and enzymes responsible for the utilization of maltose and galactose.

In addition to microorganisms, mammalian cells (eg, mammalian cells cultured in in vitro cell culture) can also be used to express and produce the protein of the invention (eg, polynucleotides encoding the subject protein). See Winnacker, From Genes to Clones, VCH Publishers, N.Y., N.Y. (1987). Suitable mammalian host cells include CHO cell lines, various Cos cell lines, HeLa cells, myeloma cell lines, and transformed B cells or hybridomas. Expression vectors used for these cells may contain expression regulatory sequences such as origins of replication, promoters and enhancers (Queen et al., Immunol. Rev. 89: 49 (1986)), and necessary processing information sites, such as ribosome binding sites, RNA splice sites, polyadenylation sites, and transcription termination sequences. Examples of suitable expression regulatory sequences include promoters derived from white immunoglobulin genes, SV40, adenovirus, bovine papilloma virus, cytomegalovirus and the like. See Co et al., J. Immunol. 148: 1149 (1992).

Once synthesized (chemical or recombinant), the plasminogen or plasmin of the present invention can be purified according to standard procedures in the art, including ammonium sulfate precipitation, affinity column, column chromatography, high performance liquid chromatography (HPLC), gel electrophoresis and the like. The plasminogen or plasmin is substantially pure, for example, at least about 80% to 85% pure, at least about 85% to 90% pure, at least about 90% to 95% pure, or 98% to 99% pure or purer, for example, free of contaminants such as cell debris; macromolecules other than the plasminogen, etc. . . . .

Pharmaceutical Formulations

Therapeutic formulations may be prepared by mixing plasminogen or plasmin having required purity with optional medicinal carriers, excipients, or stabilizers (Remington's Pharmaceutical Sciences, $16^{th}$ ed., Osol, A. ed. (1980)) to form lyophilized formulations or aqueous solutions. Acceptable carriers, excipients and stabilizers are non-toxic to recipients at the employed dosages and concentrations, and include buffers such as phosphates, citrates and other organic acids; antioxidants including ascorbic acid and methionine; preservatives (e.g., octadecyldimethylbenzylammonium chloride; hexanediamin chloride; benzalkonium chloride, benzoxonium chloride; phenol, butanol or benzyl alcohol; alkyl p-hydroxybenzoates such as methyl or propyl p-hydroxybenzoate; catechol; resorcinol; cyclohexanol; 3-pentanol; m-cresol); low molecular weight polypeptides (less than about 10 residues); proteins such as serum albumin, gelatin or immunoglobulins; hydrophilic polymers such as polyvinylpyrrolidone; amino acids such as glycine, glutamine, asparagine, histidine, arginine or lysine; monosaccharides, disaccharides and other carbohydrates including glucose, mannose, or dextrin; chelating agents such as EDTA; saccharides such as sucrose, mannitol, fucose, or sorbitol; salt foring counter ions such as sodium; metal complexes (e.g., zinc-protein complex); and/or non-ionic surfactants such as TWEEN™, PLURONICS™ or polyethylene glycol (PEG).

Formulations of the present invention may also contain one or more active compounds required for specific conditions to be treated, preferably those that are complementary in activity and have no side effects with each other, for example, anti-tumor drugs, anti-cancer drugs, anti-infective drugs, immune enhancers, pain killers, nutrients, antidotes, etc. . . . .

Plasminogen or plasmin of the present invention may be encapsulated in microcapsules prepared by, such as, coacervation technology or interfacial polymerization. For example, it can be placed in a colloidal pharmaceutical delivery system (e.g., liposomes, albumin microspheres, microemulsions, nanoparticles and nanocapsules) or placed in hydroxymethylcellulose or gel-microcapsules and poly-(methyl methacrylate) microcapsules in macroemulsions. These techniques are disclosed in Remington's Pharmaceutical Sciences $16^{th}$ edition, Osol, A. Ed. (1980).

Plasminogen or plasmin of the present invention for in vivo administration must be sterile. This can be easily achieved by filtration through a sterile filter before or after freeze drying and re-preparation.

Plasminogen or plasmin of the present invention can be used to prepare sustained-release formulations. Suitable examples of sustained-release formulations include solid hydrophobic polymer semi-permeable matrices having certain shapes and containing glycoproteins, such as films or microcapsules. Examples of sustained-release matrices include polyesters, hydrogels (such as poly(2-hydroxyethyl-methacrylate) (Langer et al., J. Biomed. Mater. Res., 15: 167-277 (1981); Langer, Chem. Tech., 12:98-105 (1982)) or poly(vinyl alcohol), polylactide (U.S. Pat. No. 3,773,919, EP 58,481), copolymers of L-glutamic acid and γ-ethyl-L-glutamic acid (Sidman, et al., Biopolymers 22:547 (1983)), non-degradable ethylene-vinyl acetate (Langer, et al., ibid), or degradable lactic acid-glycolic acid copolymers such as Lupron Depot™ (injectable microspheres composed of lactic acid-glycolic acid copolymer and leuprolide acetate), and poly-(−)-3-hydroxybutyric acid. Polymers such as ethylene-vinyl acetate and lactic acid-glycolic acid can release molecules for 100 days or more, while some hydrogels release proteins for a shorter time. A rational strategy for protein stabilization can be designed based on relevant mechanisms. For example, when the mechanism of agglomeration is found to be the formation of intermolecular S—S bonds through thiodisulfide interchange, stability can be achieved by modifying thiol residues, lyophilizing from acidic solutions, controlling humidity, using suitable additives, and developing specific polymer matrix compositions.

Administration and Dosage

The administration of the pharmaceutical composition of the present invention can be realized in different ways, for example, by intravenous, intraperitoneal, subcutaneous, intracranial, intrathecal, intraarterial (e.g., via carotid), intramuscular, intranasal, topical or intradermal administration or spinal cord or brain delivery. Aerosol formulations such as nasal spray formulations include purified aqueous or other solutions of active agents and preservatives and other isotonic agents. Such formulations are adjusted to a pH and isotonic state compatible with the nasal mucosa.

Preparations for parenteral administration include sterile aqueous or non-aqueous solutions, suspensions and emulsions. Examples of non-aqueous solvents include propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements, etc. . . . . Preservatives and other additives may also be present, for example, antimicrobials, antioxidants, chelating agents, inert gases, etc. . . . .

Medical staff will determine the dosage regimen based on various clinical factors. As is well known in the medical field, the dose for any patient depends on a variety of factors, including the patient's body size, body surface area, age, the specific compound to be administered, gender, frequency and route of administration, overall health, and other medications administered simultaneously. The dose of the pharmaceutical composition containing plasminogen of the present invention may be, for example, about 0.0001 to 2000 mg/kg, or about 0.001 to 500 mg/kg (e.g., 0.02 mg/kg, 0.25 mg/kg, 0.5 mg/kg, 0.75 mg/kg, 10 mg/kg, 50 mg/kg, etc.) subject's body weight per day. For example, the dosage may be 1 mg/kg body weight or 50 mg/kg body weight or in the range of 1 to 50 mg/kg, or at least 1 mg/kg. Dosages above or below this exemplary range are also included in the scope of the present invention, especially considering the aforementioned factors. Intermediate dosages in the aforementioned ranges are also included in the scope of the present invention. A subject is administered such doses daily, every other day, weekly or any other schedule determined by empirical analysis. Exemplary dosage schedules include 1 to 10 mg/kg for consecutive days. In the drug administration process of the present invention, real-time evaluation and periodic evaluation of the therapeutic effects and safety of radioactive and chemical injuries and related diseases are required.

Therapeutic Efficacy and Treatment Safety

One embodiment of the present invention relates to the judgment of therapeutic efficacy and treatment safety after treating a subject with plasminogen or plasmin. Methods for judging the therapeutic efficacy include, but are not limited to: 1) examination of recovery of the immune system, specifically, for example, recovery of leukocyte and platelet count, and the subject being expected to recover to normal range or improve after receiving the plasminogen or plasmin treatment of the present invention, such as leukocytes recovering to 4 to $10 \times 10^9$/L and platelets recovering to 100 to $300 \times 10^9$/L; 2) improvement of the poor performance of the digestive system, including improved anorexia, nausea, vomiting, diarrhea, constipation and other symptoms; 3) improvement of functions of various organs of the organism, including improvement of liver function such as alanine aminotransferase (ALT), total bilirubin level, renal function, etc., specifically, the subject being expected to return to normal range or improve after receiving the plasminogen or plasmin treatment of the present invention, for example, alanine aminotransferase (ALT): 0 to 40 μ/L, total bilirubin: 3.4 to 20.5 μmol/L; 4) amelioration of phlebitis, ulcers and other symptoms. In addition, the present invention also relates to the judgment of the safety of the therapeutic regimen in the process of treatment and after treatment of a subject using plasminogen or plasmin, including but not limited to counting the subject's serum half-life, half-life of treatment, medium toxic dose (TD50), median lethal dose (LD50), or observing various adverse events such as sensitization reactions occurred during or after treatment.

Articles of Manufacture or Kits

One embodiment of the present invention relates to an article of manufacture or a kit containing plasminogen or plasmin of the present invention for treating radiation damage and chemical damage and related diseases. The article preferably includes a container, label or package insert. Suitable containers include bottles, vials, syringes, etc. . . . . The container may be made of various materials such as glass or plastic. The container contains a composition that is effective for treating a disease or disorder of the invention and has a sterile access (for example, the container may be an intravenous solution bag or vial containing a stopper that can be pierced by a hypodermic injection needle). At least one active agent in the composition is plasminogen or plasmin. The container or the attached label indicates that the composition is used to treat the radioactive and chemical damage and related diseases of the present invention. The article may further include a second container containing a pharmaceutically acceptable buffer, such as phosphate buffered saline, Ringer's solution and dextrose solution. It may further include other substances required from a commercial and user perspective, including other buffers, diluents, filters, needles and syringes. In addition, the article contains a package insert with instructions for use, including, for example, instructing a user of the composition to administer a plasminogen or plasmin composition and other medications for treating accompanying diseases to a patient.

EXAMPLES

Figure 1:
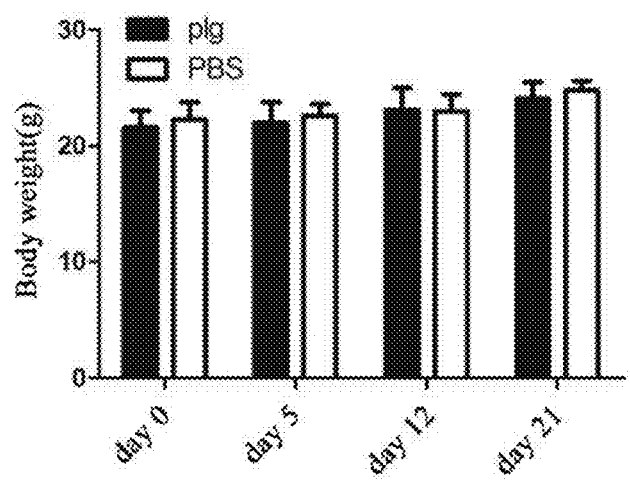
FIG. 1 shows a change in body weight of mice irradiated with 5.0 Gy X-ray after administration of plasminogen.

Materials and Methods:
Radiation Damage Model:
Experimental Animals:
SPF level healthy male C57 mice of 7 to 8 weeks old were used to study histopathological changes of organs such as spleen, liver and kidney after 5.0 Gy irradiation. The animals were randomly divided into three groups, blank control group, simple irradiation group, and plasminogen administration group after 7 days of adaptive feeding.
Experimental Method:
A linear accelerator 6 MV X-ray 5.0 Gy was used to irradiate mice uniformly of the whole body for a single time with an absorbed dose rate of 2.0 Gy/min, the absorbed dose was 5.0 Gy which is sub-lethal dose irradiation, and this was used to study histopathological changes of organs such as spleen, liver and kidney, hematopoietic and immunological functions and free radical detection. The source skin distance was 100 cm, the irradiation area was 30 cm×30 cm, and the normal control group was covered with lead for protection. After irradiation, the mice were administered till death or were killed at a specific time, and the control group was given a corresponding volume of solvent. The general condition of the exposed mice was observed, and the histopathological changes of HE staining of liver, intestine and kidney tissues and immunohistochemical staining of F4/80 were observed under light microscope.
Observation Indexes
1. Histopathological observation of liver, intestine and kidney:
After eyes and blood were taken and the mice were killed, the spleen liver, intestine and kidney tissues were taken and fixed in 10% neutral formalin, dehydrated by gradient alcohol, transparentized in xylene, paraffin-embedded, and paraffin sectioned (sheet thickness of 5 μm). After normal HE staining, they were sealed by neutral gum and the histopathological changes were observed under microscope.
2. F4/80 immunohistochemical staining observation of liver, intestine and kidney.
Liver, intestine, and kidney were paraffin sectioned (sheet thickness of 5 μm) and immunohistochemically stained, and then expression in tissues were observed.
Chemical Damage Model:
Experimental Animals:
SPF level healthy male C57 mice of 7 to 8 weeks old were used to observe side effects of anti-cisplatin. The animals were randomly divided into three groups, blank control group, simple model group, and plasminogen administration group after 7 days of adaptive feeding.
Experimental Method:
Cisplatin group: Normal saline for cisplatin ampoule was formulated into an aqueous solution having a mass concentration of 1 mg/ml and was administered by intraperitoneal injection at 3.5 ml/kg body weight. Mice of the control group received intraperitoneal injection of an equal volume of normal saline each time. Model was made after 5 days of continuous administration, and after making the model, the treatment group was given plasminogen at 1 mg/body while the control group and the model group were given the same volume of solvent, and the animals were killed on the 7th day after the administration of plasminogen. Blood and kidney tissues were taken for index test.

Observation Indexes:
1. Weigh change curve: The body weight of the mice was measured daily before administration and the change in body weight in each group of mice was observed.
2. Kidney coefficient: After the mice were killed, the kidney tissues were immediately taken and freshly weighed to calculate the kidney coefficient [kidney coefficient Z (organ mass/body weight)×100%].
3. Kidney tissue HE observation: Kidney tissues were fixed in 10% neutral formalin, dehydrated by gradient alcohol, transparentized in xylene, paraffin-embedded, and paraffin sectioned (sheet thickness of 5 μm). After normal HE staining, they were sealed by neutral gum and the histopathological changes were observed under microscope.
4. Animal thymus coefficient and spleen coefficient: After the mice were killed, the thymuses and spleens were immediately taken and freshly weighed to calculate the thymus coefficient and spleen coefficient [organ coefficient Z (organ mass/body weight)×100%].
5. Testis and epididymis weight: After mice of each group were killed, testes and epididymides were taken and weighed for statistical analysis.
6. Testicular tissue morphology observation: After the testicular tissues were conventionally fixed, dehydrated, embedded and sectioned, HE staining was used to observe the morphological changes of the testicular tissues.

Example 1: Effect of Plasminogen on Mice Body Weight after 5.0 Gy X-Ray Irradiation In the present experiment, 10 healthy male C57 mice aged 6 to 8 weeks were randomly divided into two groups and given to the solvent PBS control group and the plasminogen administration group, 5 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The day when the experiment began was the $0^{th}$ day, and the body weights were weighed and grouped. Radiation was given and plasminogen or solvent PBS was given from the first day, and the administration period was 10 days. After the completion of the administration, the animals were observed for 11 days, and the entire experiment period was 21 days. The plasminogen administration group was administered via tail vein injection at 1 mg/0.1 mL/body/day, and the solvent PBS control group was given the same volume of PBS. The body weights of the mice were measured and recorded on the $0^{th}$, $5^{th}$, $12^{th}$, and $21^{st}$ days of the experiment.

There was no obvious difference in body weight data between the solvent PBS control group and the plasminogen administration group on the $0^{th}$, $5^{th}$, $12^{th}$, and $21^{st}$ days (FIG. 1). This shows that X-ray radiation and administration do not affect the body weights of the mice.

Example 2: Protective Effect of Plasminogen on Kidneys of Mice Irradiated with 5.0 Gy X-Rays In the present experiment, 10 healthy male C57 mice aged 6 to 8 weeks were randomly divided into two groups and given to the solvent PBS control group and the plasminogen administration group, 5 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The day when the experiment began was the $0^{th}$ day, and the body weights were weighed and grouped. Radiation was given and plasminogen or solvent PBS was given from the first day, and the administration period was 10 days. After the completion of the administration, the animals were observed for 11 days, and the entire experiment period was 21 days. The plasminogen administration group was administered via tail vein injection at 1 mg/0.1 mL/body/day, and the solvent PBS control group was given the same volume of PBS. The mice were killed and dissected on the $21^{st}$ day and the kidneys were fixed in 10% neutral formalin for 24 to 48 hours. The fixed kidney tissues were dehydrated by gradient alcohol, transparentized in xylene, and then paraffin-embedded. The thickness of tissue slices was 5 μm. The slices were dewaxed and rehydrated and stained with hematoxylin and eosin (HE staining), differentiated with 1% hydrochloric acid alcohol, returned to blue with ammonia, and dehydrated by gradient alcohol and sealed. The slices were observed under the microscope at 200 times.

Figure 2:
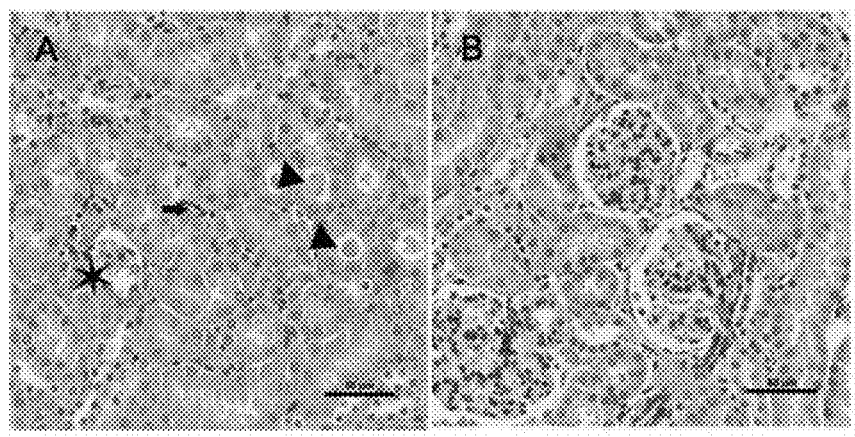
FIG. 2 shows observed result of HE staining of kidneys 10 days after administration of plasminogen in mice irradiated with 5.0 Gy X-ray.

The result showed that glomerular atrophy (*) and kidney tubular protein cast (□) were observed in the solvent PBS control group (FIG. 2A), while for the plasminogen administration group (FIG. 2B), glomerular capillary lumen was unobstructed and balloon lumen was clearly visible. The damage to the kidneys of the plasminogen administration group was notably less than that of the solvent PBS control group, which indicates that the injection of plasminogen can promote the repair of renal damage caused by X-ray radiation.

Example 3: Plasminogen Promoting Repair of Renal Inflammation in Mice Irradiated with 5.0 Gy X-Rays In the present experiment, 10 healthy male C57 mice aged 6 to 8 weeks were randomly divided into two groups and given to the solvent PBS control group and the plasminogen administration group, 5 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The day when the experiment began was the $0^{th}$ day, and the body weights were weighed and grouped. Radiation was given and plasminogen or solvent PBS was given from the first day, and the administration period was 10 days. After the completion of the administration, the animals were observed for 11 days, and the entire experiment period was 21 days. The plasminogen administration group was administered via tail vein injection at 1 mg/0.1 mL/body/day, and the solvent PBS control group was given the same volume of PBS. The mice were killed and dissected on the $21^{st}$ day and the kidneys were fixed in 10% neutral formalin for 24 to 48 hours. The fixed kidney tissues were dehydrated by gradient alcohol, transparentized in xylene, and then paraffin-embedded. The thickness of tissue slices was 5 μm. The slices were dewaxed and rehydrated and washed once. They were subjected to Tris-EDTA repair for 30 minutes, cooled at room temperature for 20 minutes and then were gently rinsed by water. They were incubated with 3% hydrogen peroxide for 15 minutes and then tissues were circled with a PAP pen. They were blocked with 10% normal goat serum (Vector laboratories, Inc., USA) for 1 hour, and then the goat serum was discarded. They were incubated at 4° C. overnight with rabbit anti-mouse F4/80 antibody (Abcam) and were washed twice by TBS, 5 minutes each time. They were incubated at secondary anti-room temperature for 1 hour with goat anti-rabbit IgG (HRP) antibody (Abcam) and were washed twice by TBS, 5 minutes each time. The color was developed by DAB kit (Vector laboratories, Inc., USA) and they were washed three times with water. Then they were stained with hematoxylin for 30 seconds and rinsed with water for 5 minutes. They were dehydrated in gradient, transparentized and sealed. The slices were observed under the microscope at 200 times.

Figure 3:
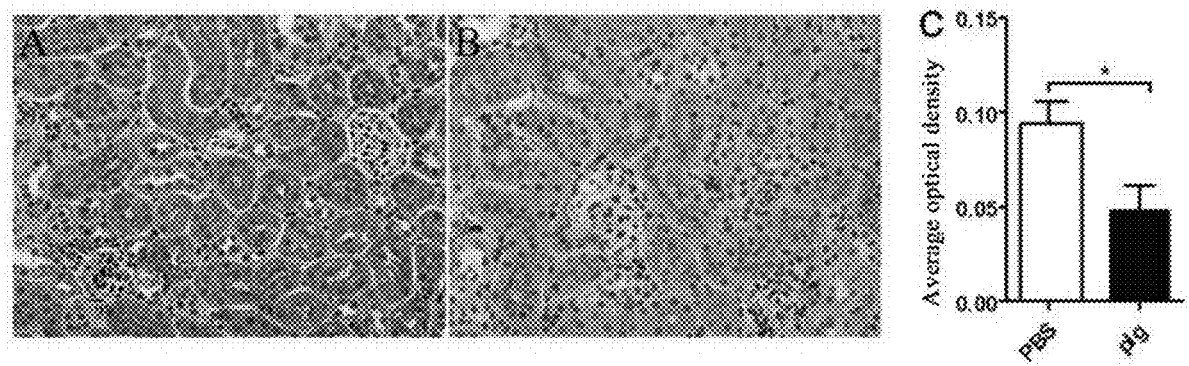
FIG. 3 shows observed result of immunohistochemical staining of macrophage marker F4/80 of kidneys 10 days after administration of plasminogen in mice irradiated with 5.0 Gy X-ray.

The F4/80 macrophage marker can indicate the degree and stage of an inflammatory reaction. The result showed that the expression level of mouse macrophage marker F4/80 in the solvent PBS control group (FIG. 3A) was higher than that in the plasminogen administration group (FIG. 3B), indicating that inflammation of the kidney tissues of animals was significantly reduced after plasminogen was given. Quantitative analysis results were consistent with microscopic observations and statistical differences were significant (FIG. 3C), which indicates that plasminogen can promote repair of renal inflammation caused by X-ray radiation.

Example 4: Protective Effect of Plasminogen on Duodenum of Mice Irradiated with 5.0 Gy X-Rays In the present experiment, 10 healthy male C57 mice aged 6 to 8 weeks were randomly divided into two groups and given to the solvent PBS control group and the plasminogen administration group, 5 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The day when the experiment began was the 0th day, and the body weights were weighed and grouped. Radiation was given and plasminogen or solvent PBS was given from the first day, and the administration period was 10 days. After the completion of the administration, the animals were observed for 11 days, and the entire experiment period was 21 days. The plasminogen administration group was administered via tail vein injection at 1 mg/0.1 mL/body/day, and the solvent PBS control group was given the same volume of PBS. The mice were killed and dissected on the $21^{st}$ day and the duodenums were fixed in 10% neutral formalin for 24 to 48 hours. The fixed duodenum tissues were dehydrated by gradient alcohol, transparentized in xylene, and then paraffin-embedded. The thickness of tissue slices was 5 μm. The slices were dewaxed and rehydrated and stained with hematoxylin and eosin (HE staining), differentiated with 1% hydrochloric acid alcohol, returned to blue with ammonia, and dehydrated by gradient alcohol and sealed. The slices were observed under the microscope at 200 times.

Figure 4:
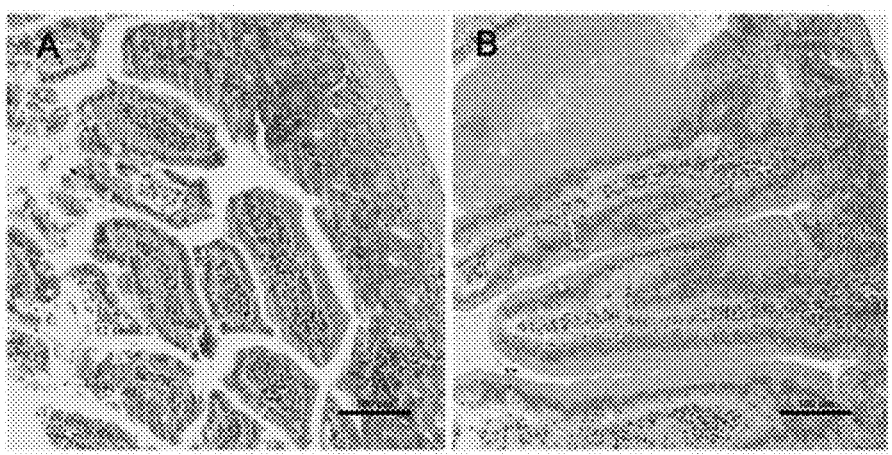
FIG. 4 shows observed result of HE staining of duodenum 10 days after administration of plasminogen in mice irradiated with 5.0 Gy X-ray.

The result showed that for the solvent PBS control group (FIG. 4A), local intestinal mucosal epithelium was detached and degenerated to necrosis, and normal mucosal structure at the detached place disappeared, while for the plasminogen administration group (FIG. 4B), red-stained refractive striated border was visible, goblet cells were visible on the mucosal epithelium, the villi center was lamina propria with a clear structure and distinct layers. The damage to the duodenums of the plasminogen administration group was notably less than that of the solvent PBS control group, which indicates that the injection of plasminogen can promote the repair of duodenal damage caused by X-ray radiation.

Example 5: Plasminogen Promoting Repair of Duodenal Inflammation in Mice Irradiated with 5.0 Gy X-Rays In the present experiment, 10 healthy male C57 mice aged 6 to 8 weeks were randomly divided into two groups and given to the solvent PBS control group and the plasminogen administration group, 5 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The day when the experiment began was the $0^{th}$ day, and the body weights were weighed and grouped. Radiation was given and plasminogen or solvent PBS was given from the first day, and the administration period was 10 days. After the completion of the administration, the animals were observed for 11 days, and the entire experiment period was 21 days. The plasminogen administration group was administered via tail vein injection at 1 mg/0.1 mL/body/day, and the solvent PBS control group was given the same volume of PBS. The mice were killed and dissected on the $21^{st}$ day and the duodenums were fixed in 10% neutral formalin for 24 to 48 hours. The fixed duodenum tissues were dehydrated by gradient alcohol, transparentized in xylene, and then paraffin-embedded. The thickness of tissue slices was 5 μm. The slices were dewaxed and rehydrated and washed once. They were subjected to Tris-EDTA repair for 30 minutes, cooled at room temperature for 20 minutes and then were gently rinsed by water. They were incubated with 3% hydrogen peroxide for 15 minutes and then tissues were circled with a PAP pen. They were blocked with 10% normal goat serum (Vector laboratories, Inc., USA) for 1 hour, and then the goat serum was discarded. They were incubated at 4° C. overnight with rabbit anti-mouse F4/80 antibody (Abeam) and were washed twice by TBS, 5 minutes each time. They were incubated at secondary anti-room temperature for 1 hour with goat anti-rabbit IgG (HRP) antibody (Abeam) and were washed twice by TBS, 5 minutes each time. The color was developed by DAB kit (Vector laboratories, Inc., USA) and they were washed three times with water. Then they were stained with hematoxylin for 30 seconds and rinsed with water for 5 minutes. They were dehydrated in gradient, transparentized and sealed. The slices were observed under the microscope at 200 times.

Figure 5:
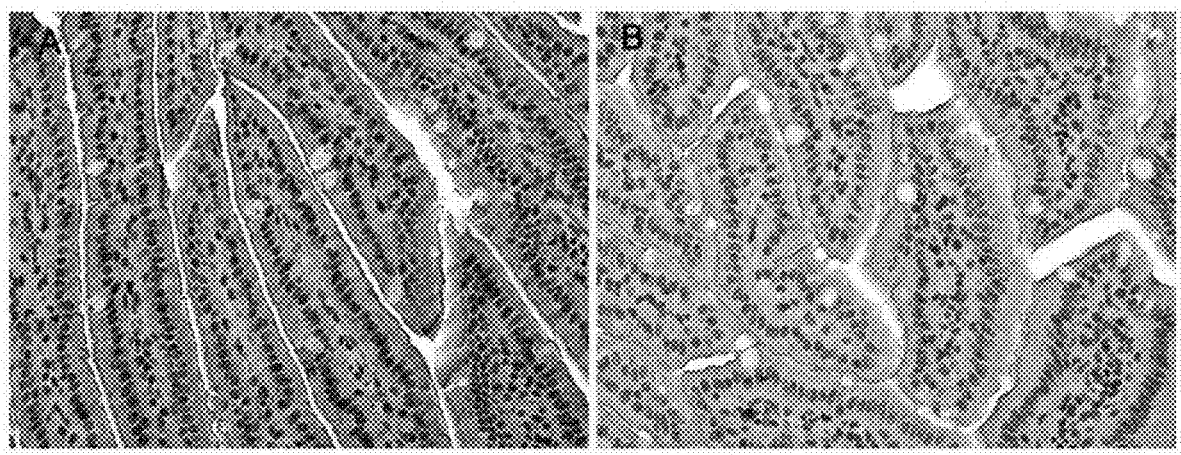
FIG. 5 shows observed result of immunohistochemical staining of macrophage marker F4/80 of duodenum 10 days after administration of plasminogen in mice irradiated with 5.0 Gy X-ray.

The result showed that the expression level of mice F4/80 in the solvent PBS control group (FIG. 5A) was higher than that in the plasminogen administration group (FIG. 5B), which indicates that inflammation of the duodenums was significantly reduced after plasminogen was given, showing that plasminogen can promote repair of duodenal inflammation caused by X-ray radiation.

Example 6: Plasminogen Promoting Repair of Liver Inflammation in Mice Irradiated with 5.0 Gy X-Rays In the present experiment, 10 healthy male C57 mice aged 6 to 8 weeks were randomly divided into two groups and given to the solvent PBS control group and the plasminogen administration group, 5 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The day when the experiment began was the $0^{th}$ day, and the body weights were weighed and grouped. Radiation was given and plasminogen or solvent PBS was given from the first day, and the administration period was 10 days. After the completion of the administration, the animals were observed for 11 days, and the entire experiment period was 21 days. The plasminogen administration group was administered via tail vein injection at 1 mg/0.1 mL/body/day, and the solvent PBS control group was given the same volume of PBS. The mice were killed and dissected on the $21^{st}$ day and the livers were fixed in 10% neutral formalin for 24 to 48 hours. The fixed liver tissues were dehydrated by gradient alcohol, transparentized in xylene, and then paraffin-embedded. The thickness of tissue slices was 5 μm. The slices were dewaxed and rehydrated and washed once. They were subjected to Tris-EDTA repair for 30 minutes, cooled at room temperature for 20 minutes and then were gently rinsed by water. They were incubated with 3% hydrogen peroxide for 15 minutes and then tissues were circled with a PAP pen. They were blocked with 10% normal goat serum (Vector laboratories, Inc., USA) for 1 hour, and then the goat serum was discarded. They were incubated at 4° C. overnight with rabbit anti-mouse F4/80 antibody (Abcam) and were washed twice by TBS, 5 minutes each time. They were incubated at secondary anti-room temperature for 1 hour with goat anti-rabbit IgG (HRP) antibody (Abcam) and were washed twice by TBS, 5 minutes each time. The color was developed by DAB kit (Vector laboratories, Inc., USA) and they were washed three times with water. Then they were stained with hematoxylin for 30 seconds and rinsed with water for 5 minutes. They were dehydrated in gradient, transparentized and sealed. The slices were observed under the microscope at 200 times.

Figure 6:
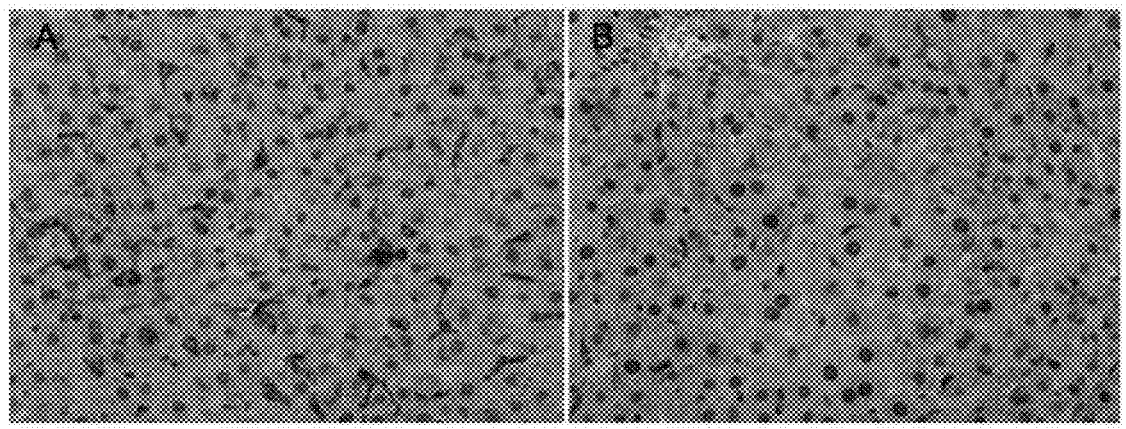
FIG. 6 shows observed result of immunohistochemical staining of macrophage marker F4/80 of livers 10 days after administration of plasminogen in mice irradiated with 5.0 Gy X-ray.
Figure 7:
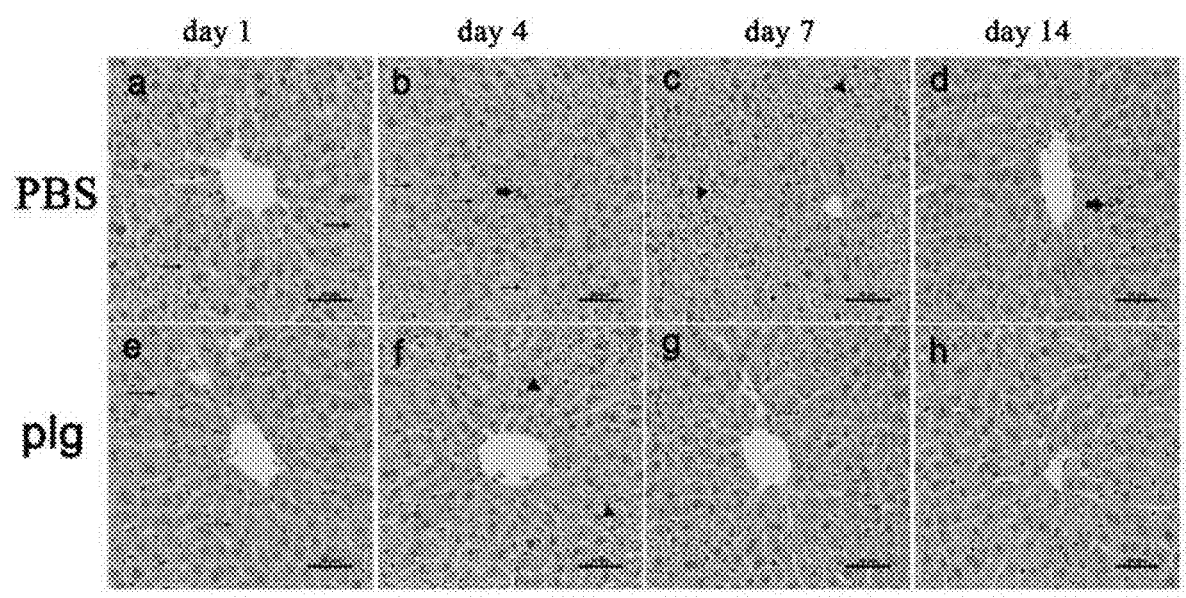
FIG. 7 shows observed results of HE staining of livers 1, 4, 7 and 14 days after administration of plasminogen in mice irradiated with 5.0 Gy X-ray.

The F4/80 immunohistochemical result showed that the expression level of mouse macrophage marker F4/80 in the solvent PBS control group (FIG. 6A) was higher than that in the plasminogen administration group (FIG. 6B) after the irradiation with 5.0 Gy X-ray and the establishment of the model, which indicates that inflammation of the liver tissues of the animals was significantly reduced after plasminogen was given.

Example 7: Protective Effect of Plasminogen on Livers of Mice Irradiated with 5.0 Gy X-Rays In the present experiment, 24 healthy male C57 mice aged 6 to 8 weeks were randomly divided into two groups and given to the solvent PBS control group and the plasminogen administration group, 12 mice for each group. After grouping, a radiation damage model was established and a linear accelerator 6 MV X-ray 5.0 Gy was used to irradiate mice uniformly of the whole body for a single time with an absorbed dose rate of 2.0 Gy/min, and the absorbed dose was 5.0 Gy (irradiation for 2.5 minutes). After the model was established, plasminogen was given within 3 hours. The plasminogen administration group was administered via tail vein injection at 1 mg/0.1 mL/body/day, and the solvent PBS control group was given the same volume of PBS. The day when the experiment began was the $0^{th}$ day, and the body weights were weighed and grouped. Radiation was given and plasminogen or solvent PBS was given from the first day, and the administration period was 14 days. 3 animals were killed respectively on the first day, the $4^{th}$ day, the $7^{th}$ day and the $14^{th}$ day after irradiation. The livers of the mice were fixed in 10% neutral formalin for 24 to 48 hours. The fixed liver tissues were dehydrated by gradient alcohol, transparentized in xylene, and then paraffin-embedded. The thickness of tissue slices was 5 μm. The slices were dewaxed and rehydrated and stained with hematoxylin and eosin (HE staining), differentiated with 1% hydrochloric acid alcohol, returned to blue with ammonia, and dehydrated by gradient alcohol and sealed. The slices were observed under the microscope at 200 times.

The result showed that for livers of the solvent PBS control group (FIG. 7a-d) on the first day, the hepatic cords spread radially around the central vein with regular texture and clear hepatic sinusoid, some hepatic cells were degenerated to necrosis, karyolysis was present and cytoplasm was lightly stained (←). On the $4^{th}$ day, mild inflammatory cell infiltration occurred in liver sinusoids (▼), and hepatic sinusoids narrowed. On the $7^{th}$ day, hepatocyte necrosis was further aggravated, and liver cells showed mild watery degeneration (□), cytoplasm was dissolved and hepatic cord disorders occurred. On the $14^{th}$ day, livers had improved greatly. The hepatic cords were regular and the hepatic sinusoids were clear. However, there was still a small amount of inflammatory cells infiltrating into the hepatic sinusoids near the central veins.

For the plasminogen administration group (FIG. 7e-g), on the first day, the hepatic cords were regular, the hepatic sinusoids were clear and there is a small amount of hepatocyte necrosis (←). On the $4^{th}$ day, the livers showed mild water degeneration (□) in hepatocytes around the central veins. From the $7^{th}$ day, liver lesions began to improve, the hepatic cords arranged radially centering the central veins and the hepatic sinusoids were clear. On the $14^{th}$ day, the livers also showed continuous improvement; necrosis was significantly reduced comparing with the first day, and the hepatic cords were more regular than the $7^{th}$ day.

In conclusion, in the PBS control group, the livers showed progressive damage from the first day to the $7^{th}$ day, and showed a tendency of improvement until the $14^{th}$ day, while in the administration group, the livers showed a significant improvement from the $7^{th}$ day, although the livers had a tendency of damage from the first day to the $4^{th}$ day. This indicates that plasminogen can promote the repair of liver damage caused by X-ray radiation.

Figure 8:
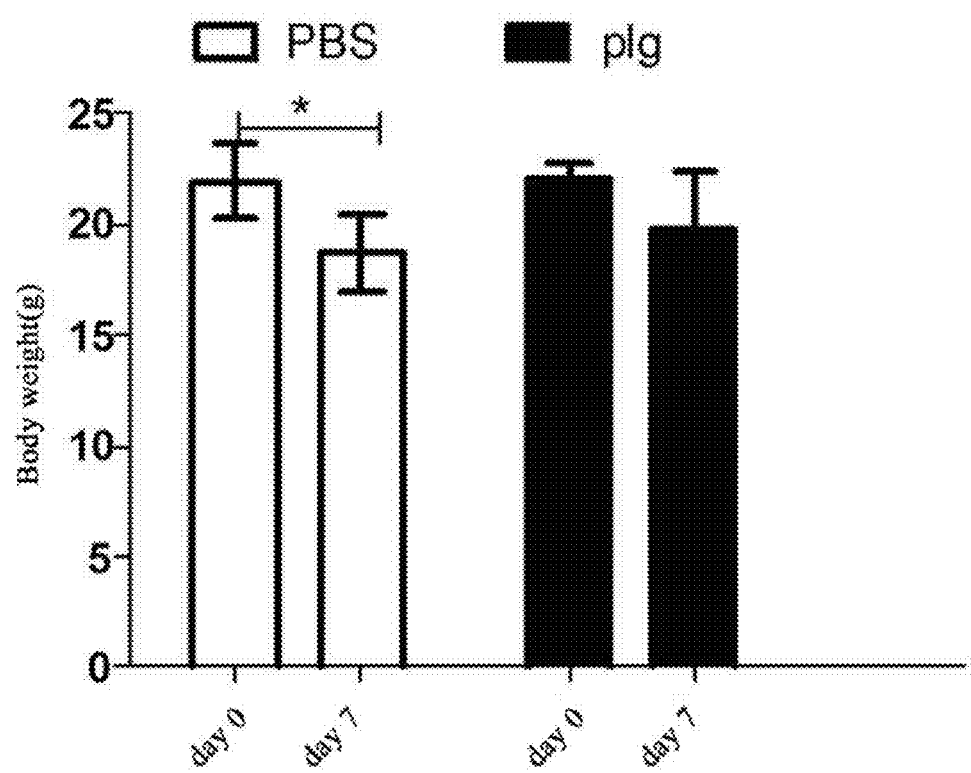
FIG. 8 shows a change in body weight of 10 mg/kg cisplatin-chemotherapy-injured model mice 7 days after administration of plasminogen.

Example 8: Effect of Plasminogen on Body Weight of Cisplatin-Chemotherapy-Injured Model Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. Intraperitoneal injection of cisplatin was started on the first day, and plasminogen or solvent PBS was given within 3 hours after the model was established. The administration period was 7 days, and the body weights were measured on the $0^{th}$ and $7^{th}$ days. The result showed that the mice in the solvent PBS control group were significantly reduced in body weight and had a statistically difference, while the mice in the plasminogen administration group had reduced body weight but the reduction was not significant (FIG. 8). This indicates that plasminogen can significantly reduce the effect of chemotherapeutic drug cisplatin on animal body weight.

Example 9: Protective Effect of Plasminogen on Kidneys of Cisplatin-Chemotherapy-Injured Model Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. Intraperitoneal injection of cisplatin was started on the first day, and plasminogen or solvent PBS was given within 3 hours after the model was established. The administration period was 7 days. The mice were killed on the 8th day and the kidneys were fixed in 10% neutral formalin for 24 to 48 hours. The fixed kidney tissues were dehydrated by gradient alcohol, transparentized in xylene, and then paraffin-embedded. The thickness of tissue slices was 5 μm. The slices were dewaxed and rehydrated and stained with hematoxylin and eosin (HE staining), differentiated with 1% hydrochloric acid alcohol, returned to blue with ammonia, and dehydrated by gradient alcohol and sealed. The slices were observed under the microscope at 200 times.

Figure 9:
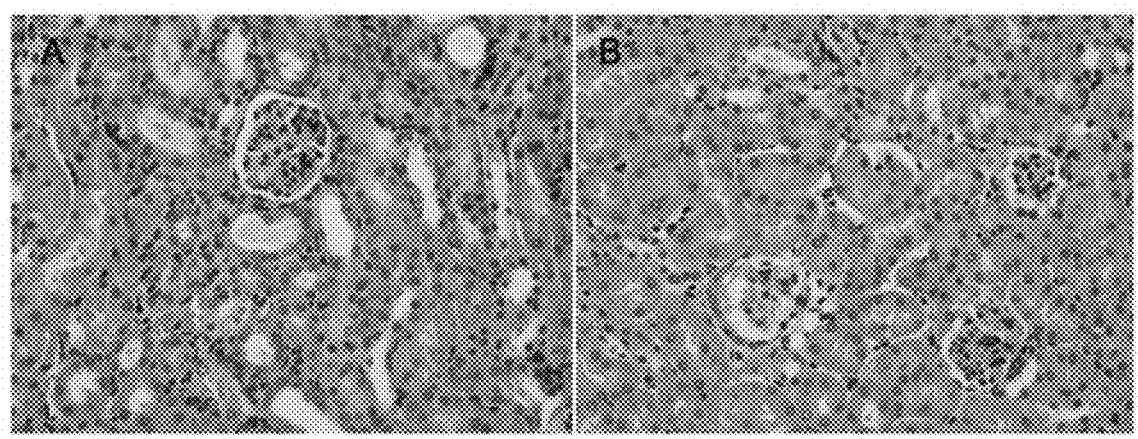
FIG. 9 shows observed result of HE staining of kidneys 7 days after administration of plasminogen in 10 mg/kg cisplatin-chemotherapy-injured model mice.

The HE result showed that tubular epithelial cell necrosis (▼) and inflammatory cell infiltration (←) were observed in the solvent PBS control group (FIG. 9A), while no significant necrosis was observed in the plasminogen administration group (FIG. 9B) and there was only a small amount of inflammatory cell infiltration. This indicates that plasminogen can reduce the kidney damage caused by chemotherapeutic drug cisplatin.

Example 10: Plasminogen Promoting Degradation of Fibrin in Kidneys of Cisplatin-Chemotherapy-Injured Model Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. Intraperitoneal injection of cisplatin was started on the first day, and plasminogen or solvent PBS was given within 3 hours after the model was established. The administration period was 7 days. The mice were killed on the 8th day and the kidneys were fixed in 10% neutral formalin for 24 to 48 hours. The fixed kidney tissues were dehydrated by gradient alcohol, transparentized in xylene, and then paraffin-embedded. The thickness of tissue slices was 5 µm. The slices were dewaxed and rehydrated and washed once. They were subjected to citric acid repair for 30 minutes, cooled at room temperature for 10 minutes and then were gently rinsed by water. They were incubated with 3% hydrogen peroxide for 15 minutes and then tissues were circled with a PAP pen. They were blocked with 10% normal goat serum (Vector laboratories, Inc., USA) for 1 hour, and then the goat serum was discarded. They were incubated at 4° C. overnight with rabbit anti-mouse fibrin antibody (Abcam) and were washed twice by TBS, 5 minutes each time. They were incubated at secondary anti-room temperature for 1 hour with goat anti-rabbit IgG (HRP) antibody (Abcam) and were washed twice by TBS, 5 minutes each time. The color was developed by DAB kit (Vector laboratories, Inc., USA) and they were washed three times with water. Then they were stained with hematoxylin for 30 seconds and rinsed with water for 5 minutes. They were dehydrated in gradient, transparentized and sealed. The slices were observed under the microscope at 200 times.

Fibrinogen is a precursor of fibrin, and in the presence of tissue damage, as a stress reaction to the body damage, fibrinogen is hydrolyzed into fibrin and deposited at the site of damage[22-24]. Therefore, damage to local fibrin level can be used as a sign of the degree of damage.

Figure 10:
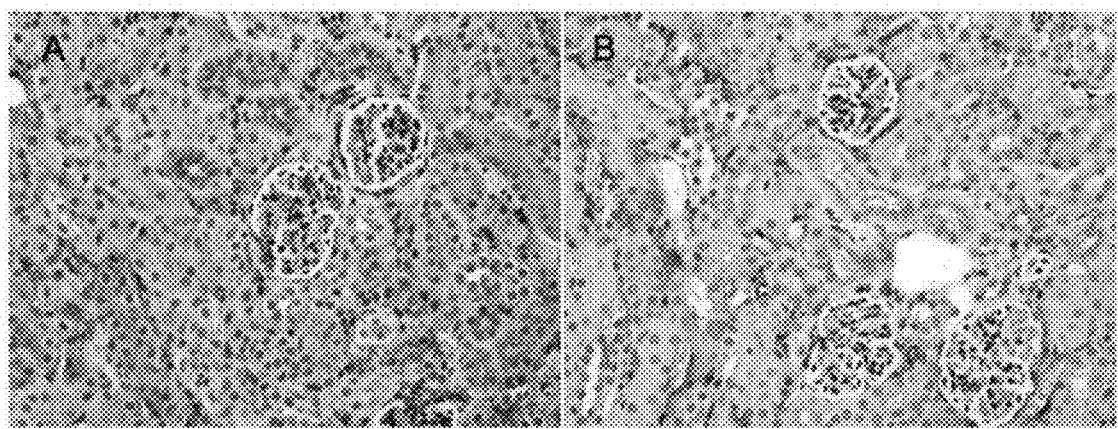
FIG. 10 shows observed result of immunohistochemical staining of fibrin in kidneys 7 days after administration of plasminogen in 10 mg/kg cisplatin-chemotherapy-injured model mice.

The result showed that the positive staining of fibrin of the solvent PBS control group (FIG. 10A) was significantly deeper than that of the plasminogen administration group (FIG. 10B). This indicates that plasminogen can significantly reduce the fibrin deposition caused by chemotherapeutic drug cisplatin, and it is helpful for the repair of renal damage caused by the chemotherapeutic drug cisplatin.

Example 11: Plasminogen Promoting the Expression of Apoptosis Inhibitory Protein Bcl-2 in Kidneys of Cisplatin-Chemotherapy-Injured Model Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. Intraperitoneal injection of cisplatin was started on the first day, and plasminogen or solvent PBS was given within 3 hours after the model was established. The administration period was 7 days. The mice were killed on the 8th day and the kidneys were fixed in 10% neutral formalin for 24 to 48 hours. The fixed kidney tissues were dehydrated by gradient alcohol, transparentized in xylene, and then paraffin-embedded. The thickness of tissue slices was 5 µm. The slices were dewaxed and rehydrated and washed once. They were subjected to citric acid repair for 30 minutes, cooled at room temperature for 10 minutes and then were gently rinsed by water. They were incubated with 3% hydrogen peroxide for 15 minutes and then tissues were circled with a PAP pen. They were blocked with 10% normal goat serum (Vector laboratories, Inc., USA) for 1 hour, and then the goat serum was discarded. They were incubated at 4° C. overnight with rabbit anti-mouse Bcl-2 antibody (Abcam) and were washed twice by TBS, 5 minutes each time. They were incubated at secondary anti-room temperature for 1 hour with goat anti-rabbit IgG (HRP) antibody (Abcam) and were washed twice by TBS, 5 minutes each time. The color was developed by DAB kit (Vector laboratories, Inc., USA) and they were washed three times with water. Then they were stained with hematoxylin for 30 seconds and rinsed with water for 5 minutes. They were dehydrated in gradient, transparentized and sealed. The slices were observed under the microscope at 200 times.

Figure 11:
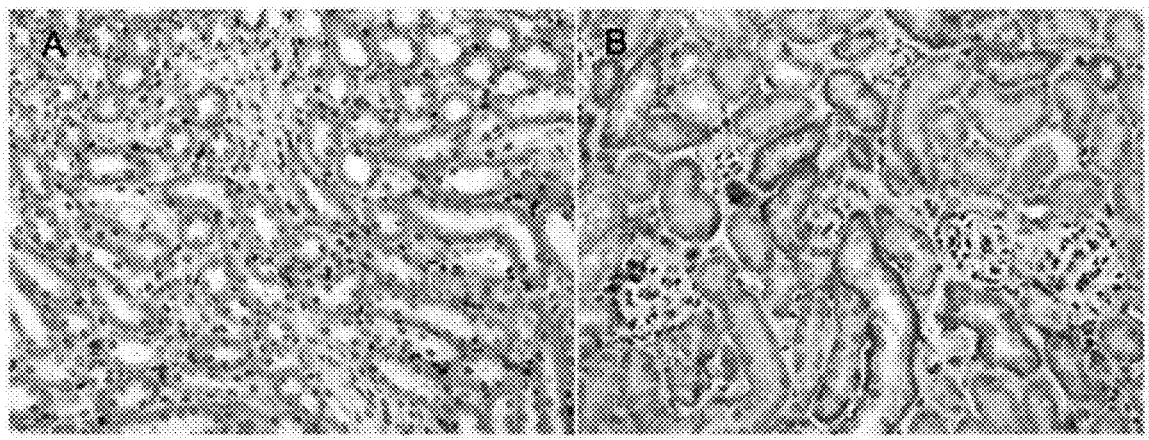
FIG. 11 shows observed result of Bcl-2 immunohistochemical staining of kidneys 7 days after administration of plasminogen in 10 mg/kg cisplatin-chemotherapy-injured model mice.

Bcl-2 is an apoptosis inhibitory protein that has down-regulation under the action of apoptosis induction[25, 26] The result showed that the positive staining of Bcl-2 in kidney tissues of the solvent PBS control group (FIG. 11A) was significantly lower than that of the plasminogen administration group (FIG. 11B). This indicates that plasminogen can significantly increase the expression of apoptosis inhibitory protein Bcl-2 in kidney tissues caused by chemotherapeutic drug cisplatin, which helps to inhibit the apoptosis of renal tissue cells.

Example 12: Protective Effect of Plasminogen on Livers of Cisplatin-Chemotherapy-Injured Model Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. On the first day, intraperitoneal injection of cisplatin was started and plasminogen or solvent PBS was given. The administration period was 7 days. The mice were killed on the 8th day and the livers were fixed in 10% neutral formalin for 24 to 48 hours. The fixed liver tissues were dehydrated by gradient alcohol, transparentized in xylene, and then paraffin-embedded. The thickness of tissue slices was 5 µm. The slices were dewaxed and rehydrated and stained with hematoxylin and eosin (HE staining), differentiated with 1% hydrochloric acid alcohol, returned to blue with ammonia, and dehydrated by gradient alcohol and sealed. The slices were observed under the microscope at 200 times.

Figure 12:
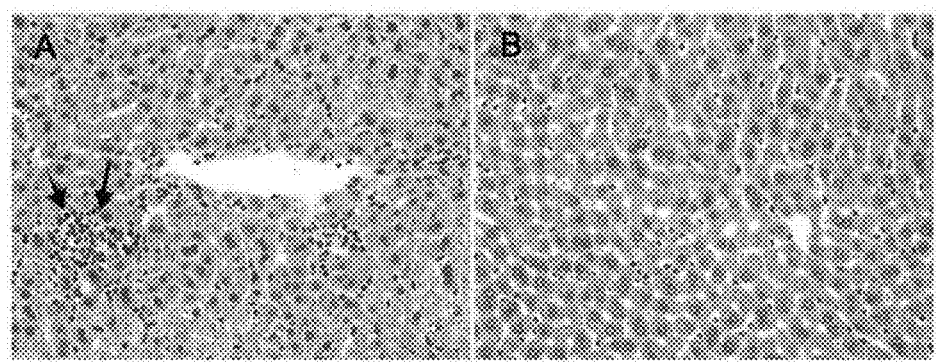
FIG. 12 shows observed result of HE staining of livers 7 days after administration of plasminogen in 10 mg/kg cisplatin-chemotherapy-injured model mice.

The HE result showed that in the solvent PBS control group (FIG. 12A), the central vein of the liver was expanded, the endothelial cells were necrotic, and the surrounding had mild inflammatory cell infiltration. Also, large inflammatory lesions were visible (←), spotty necrosis of liver cells, nuclear fragmentation, cytoplasm light staining and hepatic disorders were observed. In the plasminogen administration group (FIG. 12B), the hepatic cords of the liver were scattered around the central vein with clear hepatic sinusoids and red staining of the cytoplasm, and necrosis of hepatocytes and infiltration of inflammatory cells were significantly reduced. This indicates that plasminogen can significantly reduce the liver damage caused by chemotherapeutic drug cisplatin.

Example 13: Plasminogen Promoting Degradation of Fibrin in Livers of Cisplatin-Chemotherapy-Injured Model Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. Intraperitoneal injection of cisplatin was started on the first day, and plasminogen or solvent PBS was given within 3 hours after the model was established. The administration period was 7 days. The mice were killed on the 8th day and the livers were fixed in 10% neutral formalin for 24 to 48 hours. The fixed liver tissues were dehydrated by gradient alcohol, transparentized in xylene, and then paraffin-embedded. The thickness of tissue slices was 5 μm. The slices were dewaxed and rehydrated and washed once. They were subjected to citric acid repair for 30 minutes, cooled at room temperature for 10 minutes and then were gently rinsed by water. They were incubated with 3% hydrogen peroxide for 15 minutes and then tissues were circled with a PAP pen. They were blocked with 10% normal goal serum (Vector laboratories, Inc., USA) for 1 hour, and then the goat serum was discarded. They were incubated at 4° C. overnight with rabbit anti-mouse fibrin antibody (Abeam) and were, washed twice by TBS, 5 minutes each time. They were incubated at secondary anti-room temperature for 1 hour with goat anti-rabbit IgG (HRP) antibody (Abcam) and were washed twice by TBS, 5 minutes each time. The color was developed by DAB kit (Vector laboratories, Inc., USA) and they were washed three times with water. Then they were stained with hematoxylin for 30 seconds and rinsed with water for 5 minutes. They were dehydrated in gradient, transparentized and sealed. The slices were observed under the microscope at 200 times.

Fibrinogen is a precursor of fibrin, and in the presence of tissue damage, as a stress reaction to the body damage, fibrinogen is hydrolyzed into fibrin and deposited at the site of damage[22-24]. Therefore, damage to local fibrin level can be used as a sign of the degree of damage.

Figure 13:
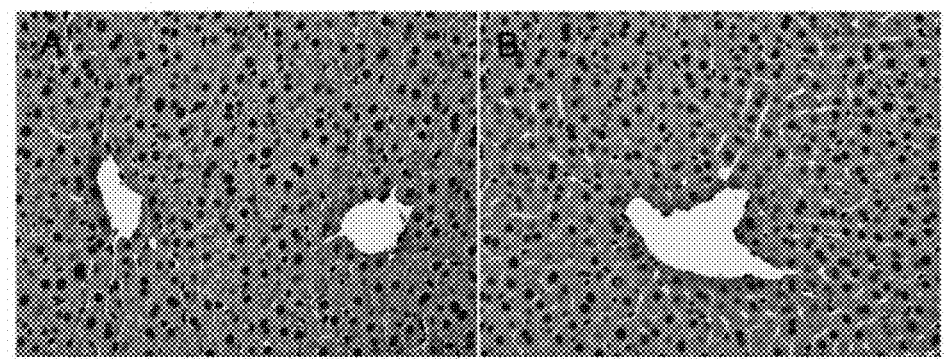
FIG. 13 shows observed result of immunohistochemical staining of fibrin in livers 7 days after administration of plasminogen in 10 mg/kg cisplatin-chemotherapy-injured model mice.

The result showed that the positive staining of fibrin in the liver tissues of the solvent PBS control group (FIG. 13A) was significantly deeper than that of the plasminogen administration group (FIG. 13B). This indicates that plasminogen can significantly reduce the fibrin deposition, which promotes the repair of liver damage caused by the chemotherapeutic drug cisplatin.

Example 14: Plasminogen Reducing Toxicity of Cisplatin Treatment on Reproductive Organs of Mice In the present experiment, 10 healthy male C57 mice aged 8 to 9 weeks were randomly divided into two groups and given to the solvent PBS control group and the plasminogen administration group, 5 mice for each group. After grouping, a chemotherapy damage model was established and cisplatin was given via intraperitoneal injection for a single time at 10 mg/Kg body weight. After the model was established, plasminogen was administered to the plasminogen administration group via tail vein injection at 1 mg/0.1 mL/body/day, and the solvent PBS control group was given the same volume of PBS. The day when the experiment began was the $0^{th}$ day, and the body weights were weighed and grouped. Intraperitoneal injection of cisplatin was started on the first day, and plasminogen or solvent PBS was given within 3 hours after the model was established. The administration period was 7 days. The mice were killed on the 8th day and the testes and epididymides were fixed in 10% neutral formalin for 24 to 48 hours. The fixed testis and epididymis tissues were dehydrated by gradient alcohol, transparentized in xylene, and then paraffin-embedded. The thickness of tissue slices was 5 μm. The slices were dewaxed and rehydrated and stained with hematoxylin and eosin (HE staining), differentiated with 1% hydrochloric acid alcohol, returned to blue with ammonia, and dehydrated by gradient alcohol and sealed. The slices were observed under the microscope at 200 times.

Figure 14:
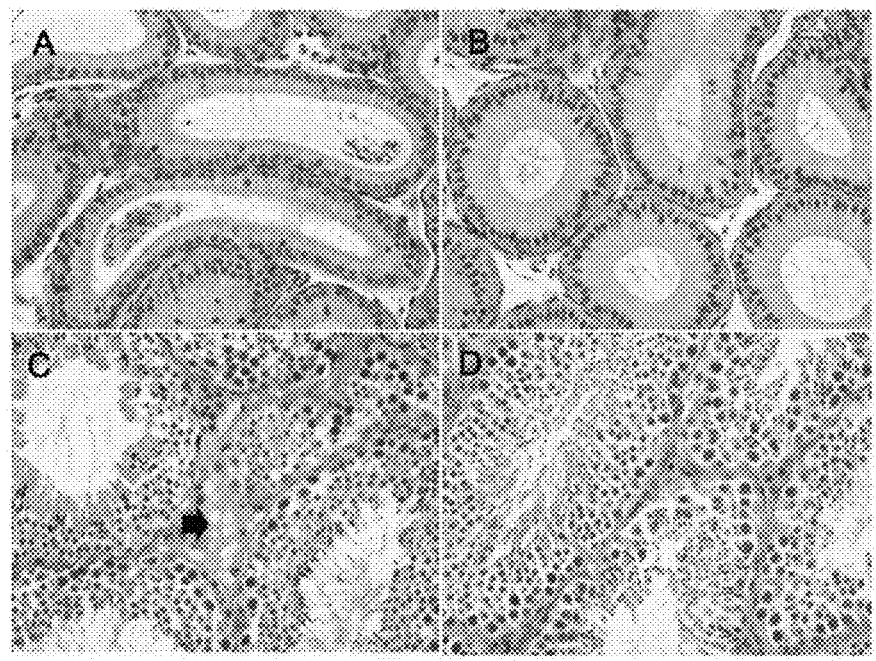
FIG. 14 shows observed result of HE staining of testes and epididymides 7 days after administration of plasminogen in 10 mg/kg cisplatin-chemotherapy-injured model mice.

The result showed that in the solvent PBS control group, the number of spermatozoa in deferent duct of epididymis (FIG. 14A) decreased, accompanied by multiple epididymal tissue necrosis, and the number of spermatozoa was significantly reduced as compared with the plasminogen administration group, and multiple interstitial necrosis of the testis (FIG. 14C) was observed. In contrast with the solvent PBS control group, the number of spermatozoa in deferent duct of epididymis in the plasminogen administration group (FIG. 14B) was also significantly greater than that of the solvent PBS control group, and testis interstitial (FIG. 14D) necrotic lesions (single necrotic lesions) were also significantly reduced. This indicates that plasminogen can reduce the toxicity to the reproductive organs caused by chemotherapeutic drug cisplatin.

REFERENCES

[1] Alexander C M and Werb, Z. (1991). Extracellular matrix degradation. In Cell Biology of Extracellular Matrix, Hay E D, ed. (New York: Plenum Press), pp. 255-302
[2] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.
[3] He, C. S., Wilhelm, S. M., Pentland, A. P., Marmer, B. L., Grant, G. A., Eisen, A. Z., and Goldberg, G. I. (1989). Tissue cooperation in a proteolytic cascade activating human interstitial collagenase. Proc. Natl. Acad Sci. U. S. A 86, 2632-2636
[4] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U. S. A 82, 4939-4943.
[5] Vassalli, J. D., Baccino, D., and Belin, D. (1985). A cellular binding site for the Mr 55,000 form of the human plasminogen activator, urokinase. J. Cell Biol. 100, 86-92.
[6] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[7] Saksela, O. and Rifkin, D. B. (1988). Cell-associated plasminogen activation: regulation and physiological functions. Annu. Rev. Cell Biol. 4, 93-126

[8] Raum, D., Marcus, D., Alper, C. A., Levey, R., Taylor, P. D., and Starzl, T. E. (1980). Synthesis of human plasminogen by the liver. Science 208, 1036-1037

[9] Wallén P (1980). Biochemistry of plasminogen. In Fibrinolysis, Kline D L and Reddy K K N, eds. (Florida: CRC

[10] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U. S. A 72, 2577-2581.

[11] Collen, D. and Lijnen, H. R. (1991). Basic and clinical aspects of fibrinolysis and thrombolysis. Blood 78, 3114-3124.

[12] Alexander, C. M. and Werb, Z. (1989). Proteinases and extracellular matrix remodeling. Curr. Opin. Cell Biol. 1, 974-982.

[13] Mignatti, P. and Rifkin, D. B. (1993). Biology and biochemistry of proteinases in tumor invasion. Physiol Rev. 73, 161-195.

[14] Collen, D. (2001). Ham-Wasserman lecture: role of the plasminogen system in fibrin-homeostasis and tissue remodeling. Hematology. (Am. Soc. Hematol. Educ. Program.) 1-9.

[15] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[16] Andreasen, P. A., Kjoller, L., Christensen, L., and Duffy, M. J. (1997). The urokinase-type plasminogen activator system in cancer metastasis: a review. Int. J. Cancer 72, 1-22.

[17] Rifkin, D. B., Mazzieri, R., Munger, J. S., Noguera, J., and Sung, J. (1999). Proteolytic control of growth factor availability. APMIS 107, 80-85.

18] Marder V J, Novokhatny V. Direct fibrinolytic agents: biochemical attributes, preclinical foundation and clinical potential[J]. Journal of Thrombosis and Haemostasis, 2010, 8(3): 433-444.

[19] Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis[J]. Progress in chemical fibrinolysis and thrombolysis, 1978, 3: 191-209.

[20] Nagai N, Demarsin E, Van Hoef B, et al. Recombinant human microplasmin: production and potential therapeutic properties[J]. Journal of Thrombosis and Haemostasis, 2003, 1(2): 307-313.

[21] Hunt J A, Petteway Jr S R, Scuderi P, et al. Simplified recombinant plasmin: production and functional comparison of a novel thrombolytic molecule with plasma-derived plasmin[J]. Thromb Haemost, 2008, 100(3): 413-419.

[22] Jae Kyu Ryu, Mark A. Petersen, Sara G Murray et al. Blood coagulation protein fibrinogen promotes autoimmunity and demyelination via chemokine release and antigen presentation. NATURE COMMUNICATIONS, 2015, 6:8164.

[23] Dimitrios Davalos, Katerina Akassoglou. Fibrinogen as a key regulator of inflammation in disease. Seminars in Immunopathology, 2012. 34(1):43-62.

[24] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.

[25] Moungjaroen J, Nimmannit U, Callery P S, Wang L, Azad N, Lipipun V, Chanvorachote P, Rojanasakul Y (2006). Reactive oxygen species mediate caspase activation and apoptosis induced by lipoic acid in human lung epithelial cancer cells through Bcl-2 downregulation. J Pharmacol Exp Ther 319, 1062-1069.

[26] Wang L, Chanvorachote P, Toledo D, Stehlik C, Mercer R R, Castranova V, Rojanasakul Y (2008). Peroxide is a key mediator of Bcl-2 down-regulation and apoptosis induction by cisplatinin human lung cancer cells. Mol Pharmacol 73, 119-127.

DRAWINGS

FIG. 1:
Weight (g)
0th day 5th day 12th day 21st day
FIG. 3:
Average optical density
FIG. 7:
1st day 4th day 7th day 14th day
FIG. 8:
Weight (g)
0th day 7th day 0th day 7th day

What is claimed is:

1. A method for treating radiation damage and chemical damage in a subject, comprising administering to the subject an effective amount of plasminogen, wherein the radiation damage and chemical damage is caused by radiotherapy, chemotherapy or chemoradiotherapy, and wherein the plasminogen has a sequence identity of at least 80%, 85%, 90%, 95%, 96%, 97%, 98% or 99% with SEQ ID NO: 2, 6, 8, 10 or 12 and has plasminogen activity.

2. The method according to claim 1, wherein the damage comprises damage to bone marrow hematopoietic system, skin, mucous membrane, immune system and reproductive system.

3. The method according to claim 1, wherein the damage comprises damage to liver, spleen, kidney, lung, gastrointestinal tract, thymus, bone marrow, testis and epididymis.

4. The method according to claim 1, wherein the damage comprises decrease in general healthy conditions, systemic side effects and local side effects.

5. The method according to claim 1, wherein the damage comprises mucosal ulcers, decreased immune function, myelosuppression, digestive dysfunction, heart, liver, spleen, lung, kidney, ovarian, testicular toxicity dysfunctions, and neurotoxicity dysfunction.

6. The method according to claim 1, wherein the plasminogen is administered in combination with one or more other drugs or therapies.

7. The method according to claim 6, wherein the other drugs or therapies comprise anti-cancer drugs, anti-infective drugs, immunopotentiators, analgesics, nutrients and antidotes.

* * * * *